US012697118B2

(12) United States Patent

Ryle

(10) Patent No.: US 12,697,118 B2

(45) Date of Patent: Aug. 4, 2026

(54) FIRING COUPLED CLOSURE AND JOINT REACTION

(71) Applicant: Cilag GmbH International, Zug (CH)

(72) Inventor: William Ryle, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 112 days.

(21) Appl. No.: 18/651,281

(22) Filed: Apr. 30, 2024

(65) Prior Publication Data

US 2025/0331855 A1 Oct. 30, 2025

(51) Int. Cl.
*A61B 17/072* (2006.01)

(52) U.S. Cl.
CPC ............... *A61B 17/07207* (2013.01); *A61B 2017/07271* (2013.01)

(58) Field of Classification Search
CPC ............ A61B 17/068; A61B 17/07207; A61B 2017/07271
See application file for complete search history.

(56) References Cited

U.S. PATENT DOCUMENTS

| | | | | |
|---|---|---|---|---|
| 9,072,535 B2 * | 7/2015 | Shelton, IV | ......... | A61B 17/105 |
| 11,304,697 B2 | 4/2022 | Fanelli et al. | | |
| 11,317,912 B2 | 5/2022 | Jenkins et al. | | |
| 11,439,391 B2 | 9/2022 | Bruns et al. | | |
| 11,883,024 B2 | 1/2024 | Bakos | | |

| | | |
|---|---|---|
| 2015/0289873 A1 | 10/2015 | Shelton, IV et al. |
| 2022/0031313 A1 | 2/2022 | Bakos et al. |
| 2022/0226049 A1 | 7/2022 | Scheib et al. |

FOREIGN PATENT DOCUMENTS

WO 2022023934 A1 2/2022

OTHER PUBLICATIONS

Annex to the Invitation to Pay Additional Fees with communication of International Search Report and Written Opinion for International Application No. PCT/IB2025/054449 mailed on Aug. 27, 2025 (13 pages).

* cited by examiner

*Primary Examiner* — Michelle Lopez
(74) *Attorney, Agent, or Firm* — Lempia Summerfield Katz LLC

(57) ABSTRACT

An end effector of a surgical instrument may be equipped with a firing redirect assembly including: a firing carrier; a reaction pulley disposed distally from the firing carrier; a firing cable coupled to a distal end of the firing carrier and wrapping around the reaction pulley and extending proximally past the firing carrier; and a reaction cable coupled to and extending between a distal end of the reaction pulley and a proximal end of an end effector of the surgical tool, the end effector including a cartridge jaw and an anvil jaw pivotably connected to the cartridge jaw at a pivot, where a firing load on the firing cable in a proximal direction causes the firing carrier to translate distally and causes the reaction pulley and the reaction cable to translate proximally, thereby assisting with closing the anvil jaw or assisting with stabilizing an articulation joint of the end effector.

20 Claims, 24 Drawing Sheets

FIRING COUPLED CLOSURE AND JOINT REACTION

BACKGROUND

A variety of surgical instruments include an end effector for use in conventional medical treatments and procedures conducted by a medical professional operator, as well as applications in robotically assisted surgeries. Such surgical instruments may be directly gripped and manipulated by a surgeon or incorporated into robotically surgical systems. In the case of robotically assisted surgery, the surgeon may operate a master controller to remotely control the motion of such surgical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller may include one or more hand input devices (such as joysticks, exoskeletal gloves, master manipulators, or the like), which are coupled by a servo mechanism to the surgical instrument. In one example, a servo motor moves a manipulator supporting the surgical instrument based on the surgeon's manipulation of the hand input devices. During the surgery, the surgeon may employ, via a robotic surgical system, a variety of surgical instruments including an ultrasonic blade, a surgical stapler, a tissue grasper, a needle driver, an electrosurgical cautery probe, etc. Each of these structures performs functions for the surgeon, for example, cutting tissue, coagulating tissue, holding or driving a needle, grasping a blood vessel, dissecting tissue, or cauterizing tissue.

In some settings, endoscopic or laparoscopic surgical instruments may be preferred over traditional open surgical devices to minimize the size of the surgical incision as well as post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft that extends proximally from the end effector to a handle (or robot attachment) portion, which is manipulated by the clinician, or alternatively to a robot. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected over one or more degrees of freedom, e.g., relative to the longitudinal axis of the shaft.

Examples of endoscopic surgical instruments include surgical staplers. Some such staplers, which may also be referred to as endocutters, are operable to clamp down on layers of tissue, cut through the clamped layers of tissue, and drive staples through the layers of tissue to substantially seal the severed layers of tissue together near the severed ends of the tissue layers. In such instruments, the knife which performs the cutting is further coupled with, or otherwise drives/pushes, either directly or indirectly, a sled which deploys the staples such that the two move together to substantially simultaneously transect and staple the clamped tissue. Such endoscopic surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. Such procedures may include the use of the stapler to sever and close a vessel leading to an organ, such as a lung. For instance, the vessels leading to an organ may be severed and closed by a stapler before removal of the organ from the thoracic cavity. Of course, surgical staplers may be used in various other settings and procedures.

In some procedures, it may be necessary to fire (i.e., cut and/or staple) along tissue where more than one firing is necessary to complete the procedure. In other words, it may be necessary to perform multiple sequential firings along a continuous path, known as "marching." With procedures that involve marching, a surgical stapler end effector may be placed at the surgical site, actuated to cut and staple, removed from the surgical site for installation of a new staple cartridge, and then placed back at the surgical site again for the next firing along the same path.

Certain endocutters, such as a two degree of freedom robotic endocutters, may use a certain type of knife, such as an "E-beam" knife, to transect tissue and control the position of the anvil relative to the cartridge deck. When the knife encounters thicker tissue, the knife must do the additional work of compressing the tissue, which generates high loads on the knife translation subsystem. These endocutters may also use a direct push firing system, which transmits the firing load directly through the articulation joint. As the firing load increases, the articulation joint reacts to the increased force. However, the reaction to the increased firing loads may negatively impact joint performance during normal operation and lead to problems, such as de-articulation.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

3

Figure 1:
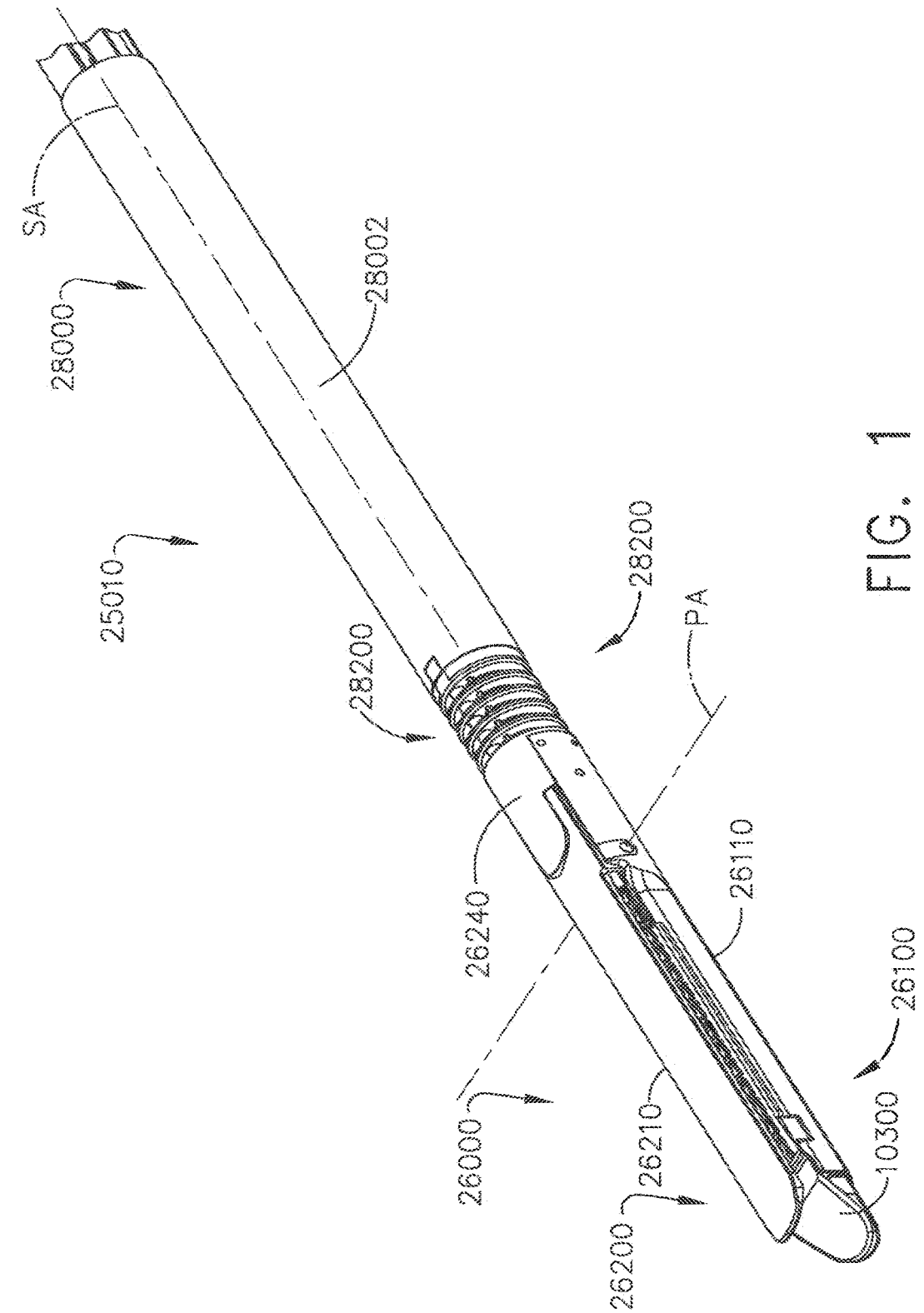
FIG. 1 is a perspective view of a portion of another surgical instrument embodiment.
Figure 2:
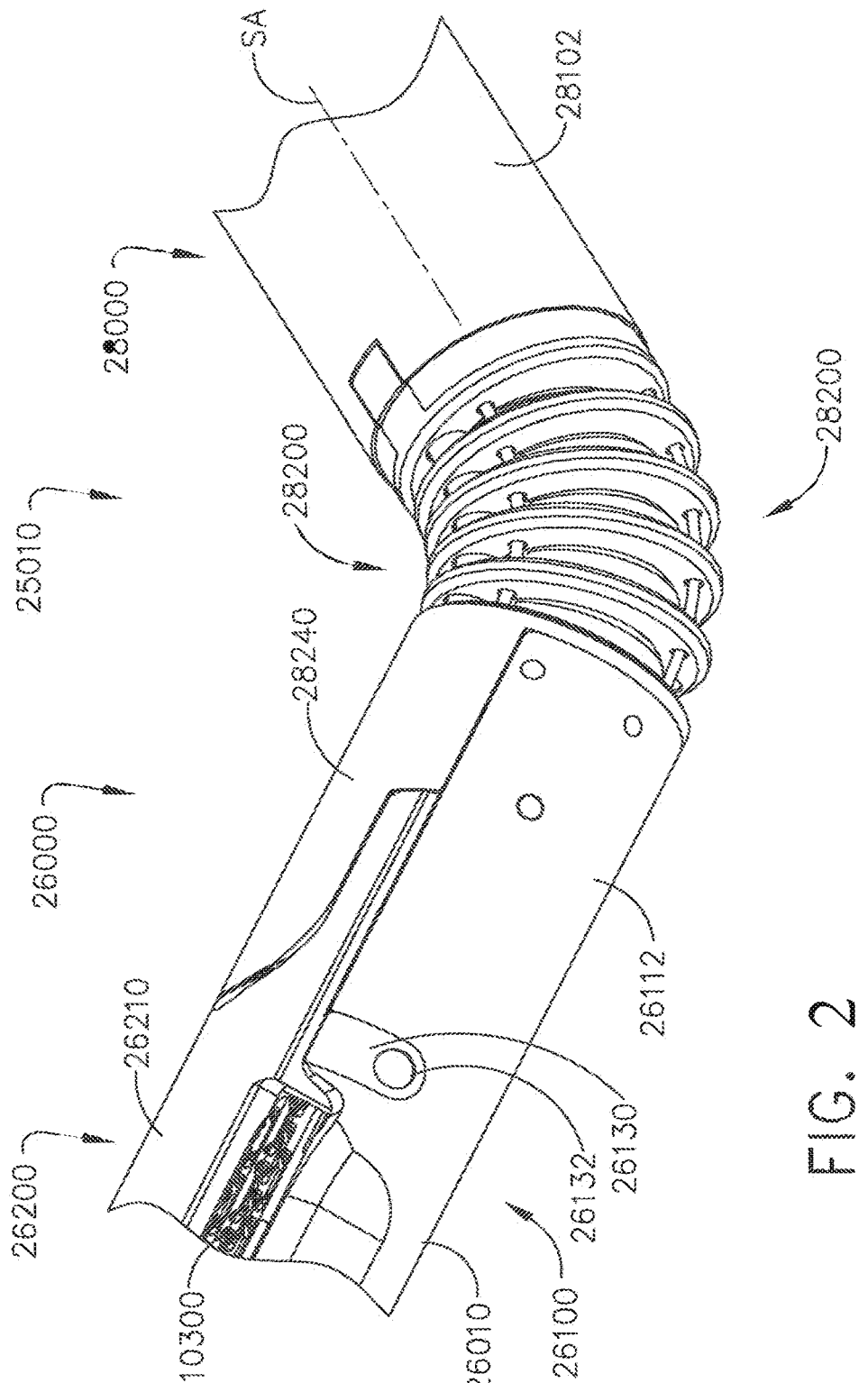
FIG. 2 is a perspective view of a portion of the surgical instrument of FIG. 1 with a surgical end effector portion thereof in an articulated position relative to an elongate shaft portion thereof.
Figures 3, 4:
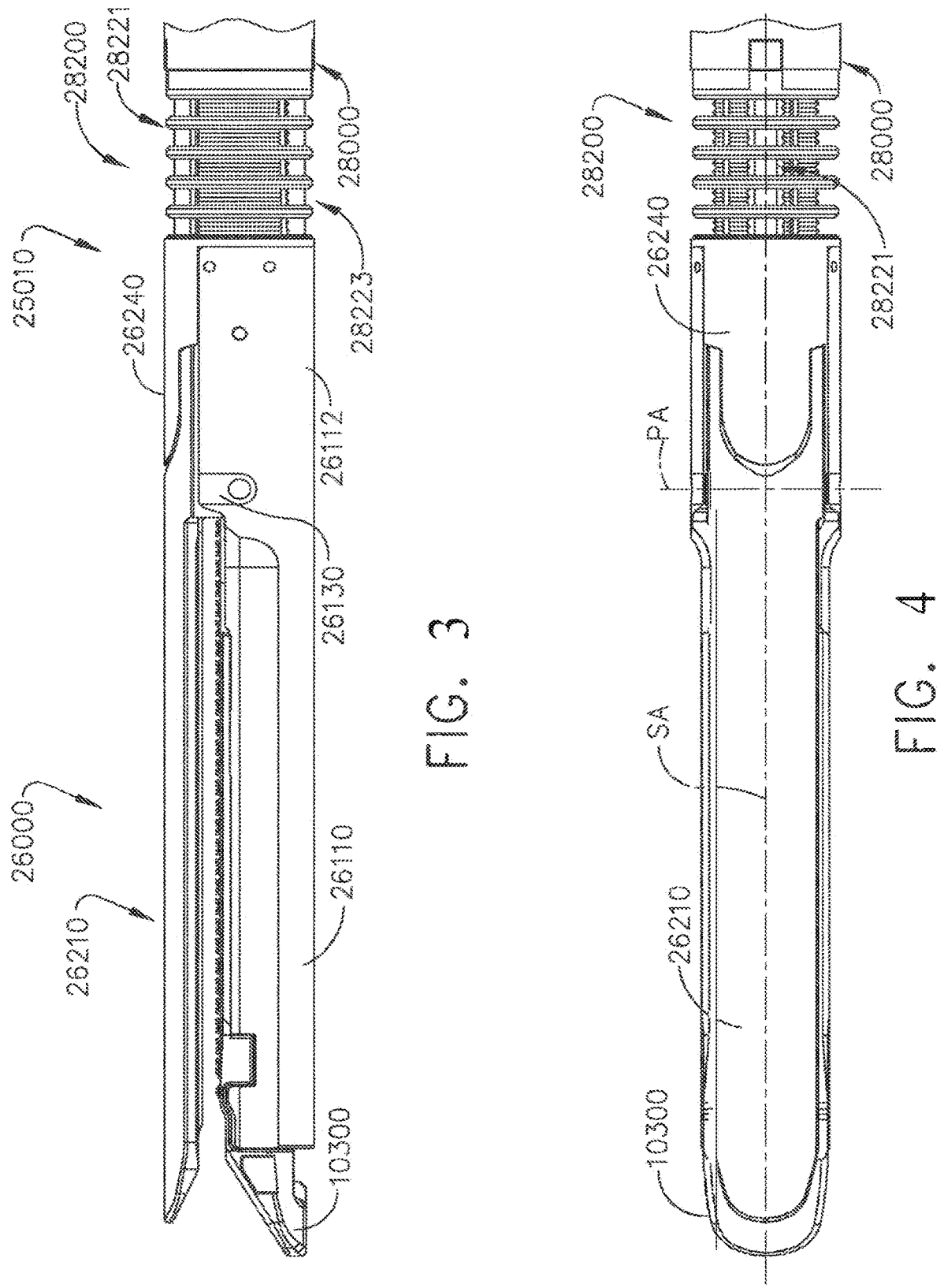
FIG. 3 is a side elevational view of the surgical end effector of FIG. 2, with an anvil thereof in a closed position.
FIG. 4 is a top view of the surgical end effector of FIG. 3.
Figures 8, 9:
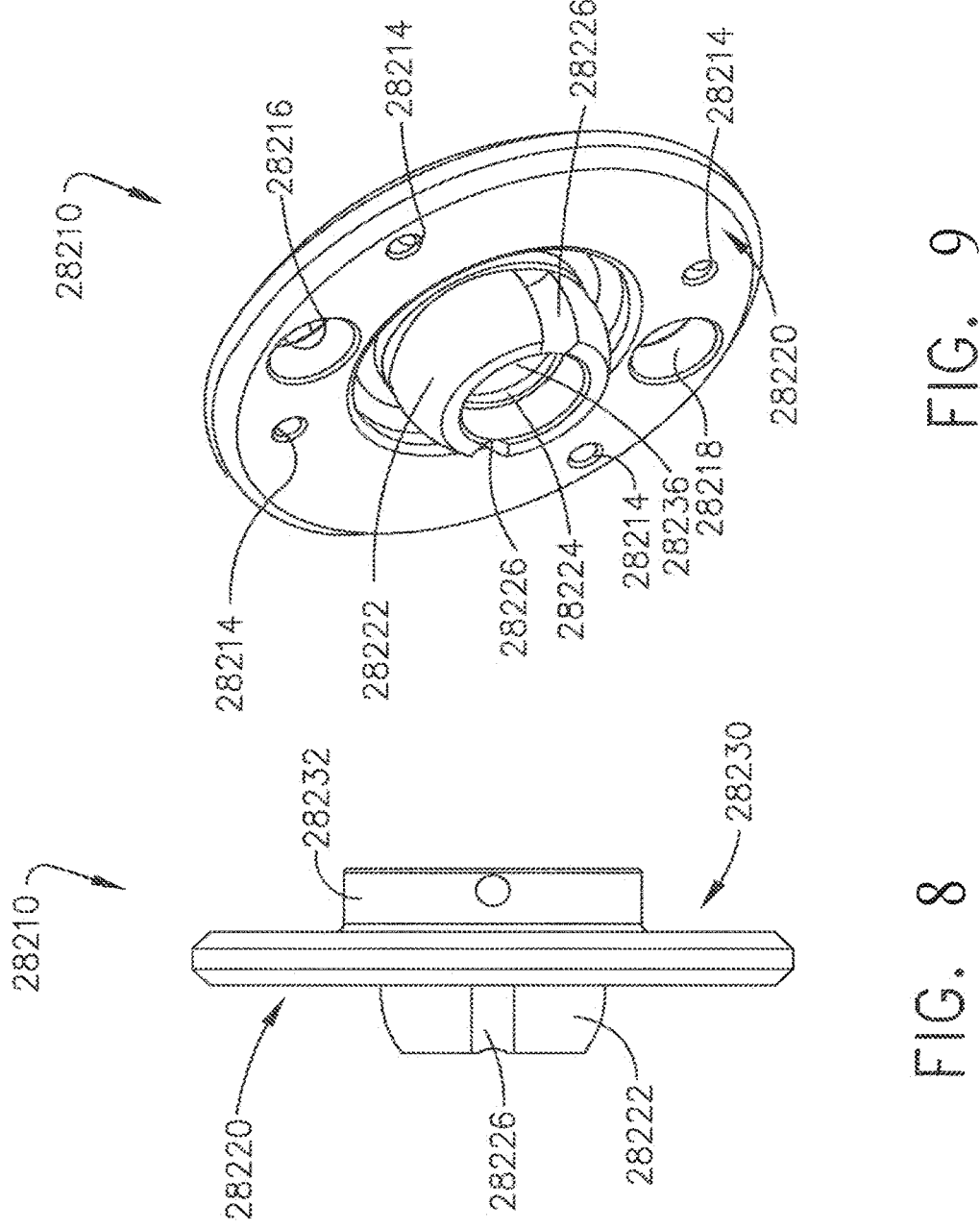
FIG. 8 is a side view of an annular disc member of the articulation joint of FIG. 7.
FIG. 9 is a perspective view of the annular disc member of FIG. 8.
Figures 10, 11:
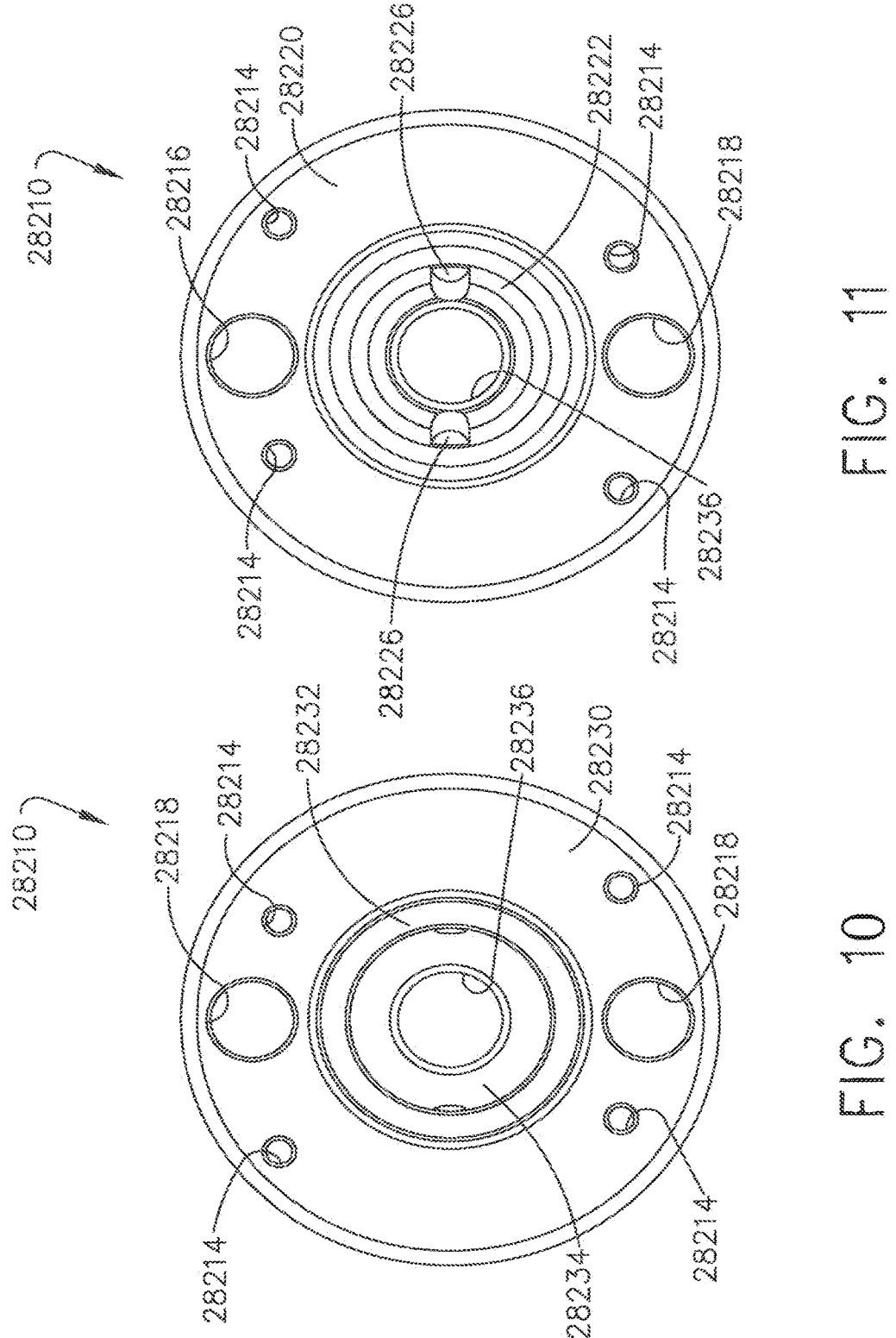
FIG. 10 is a view of a distal face of the annular disc member of FIG. 8.
Figure 12:
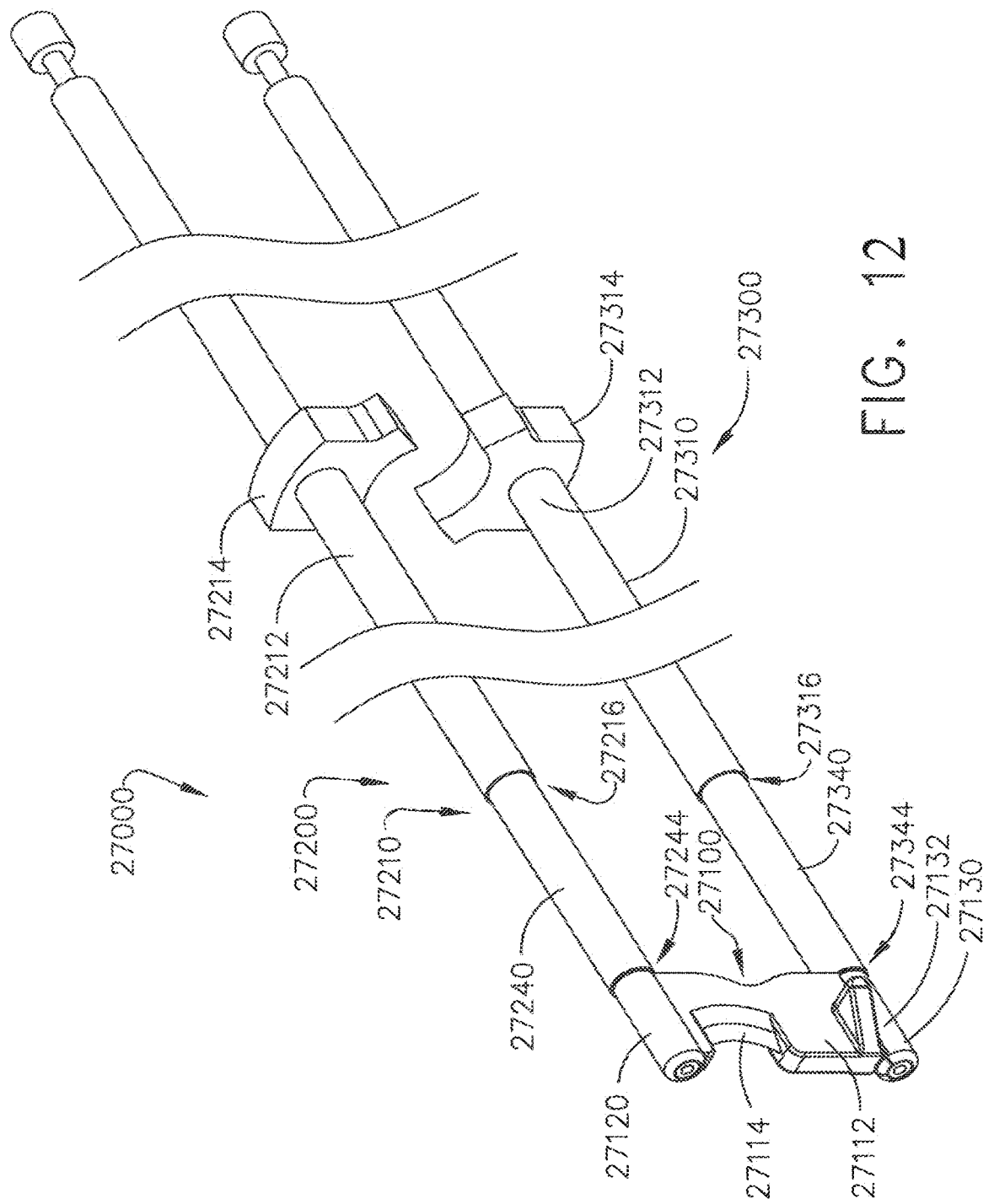
Figure 13:
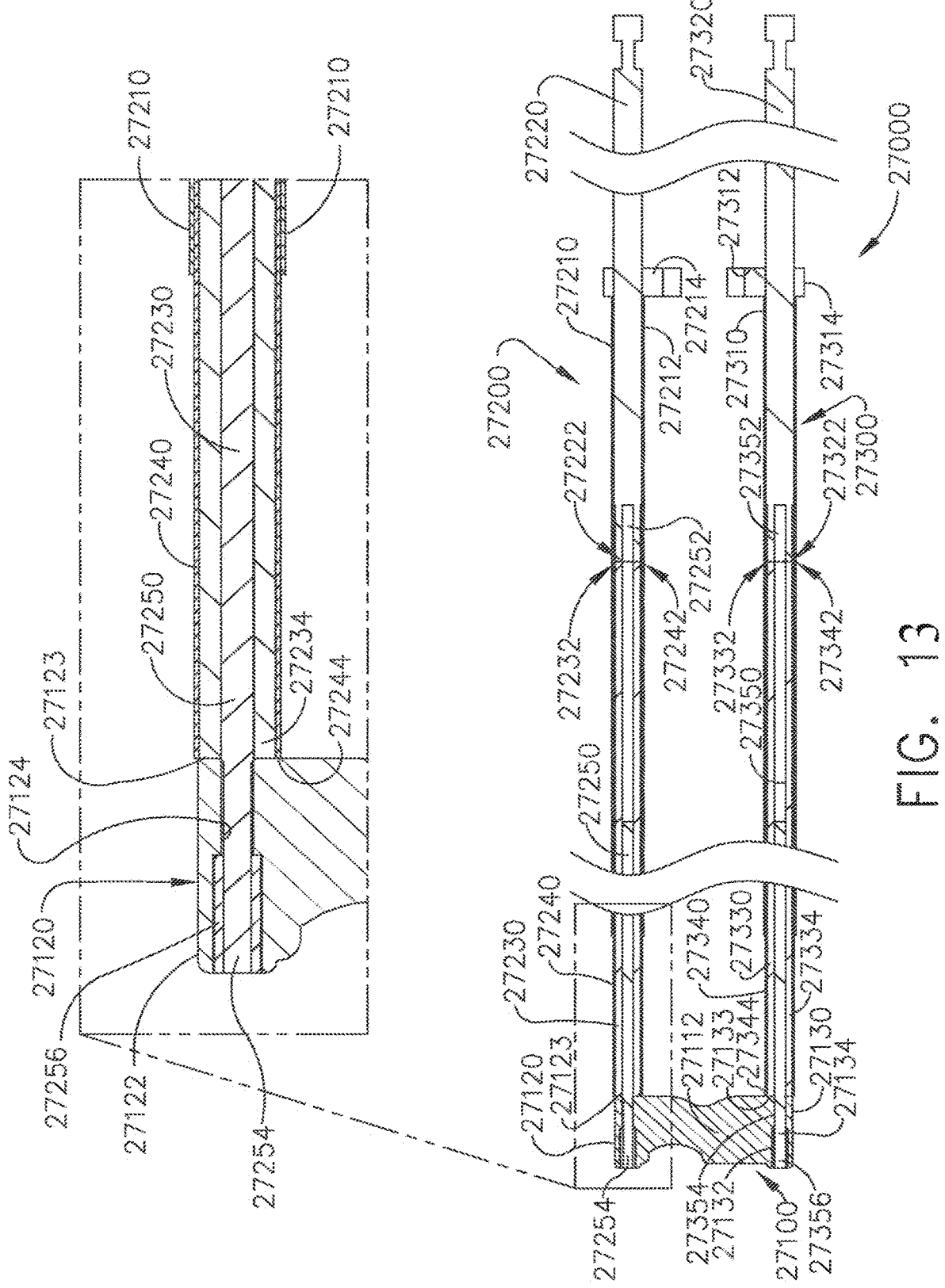
Figure 14:
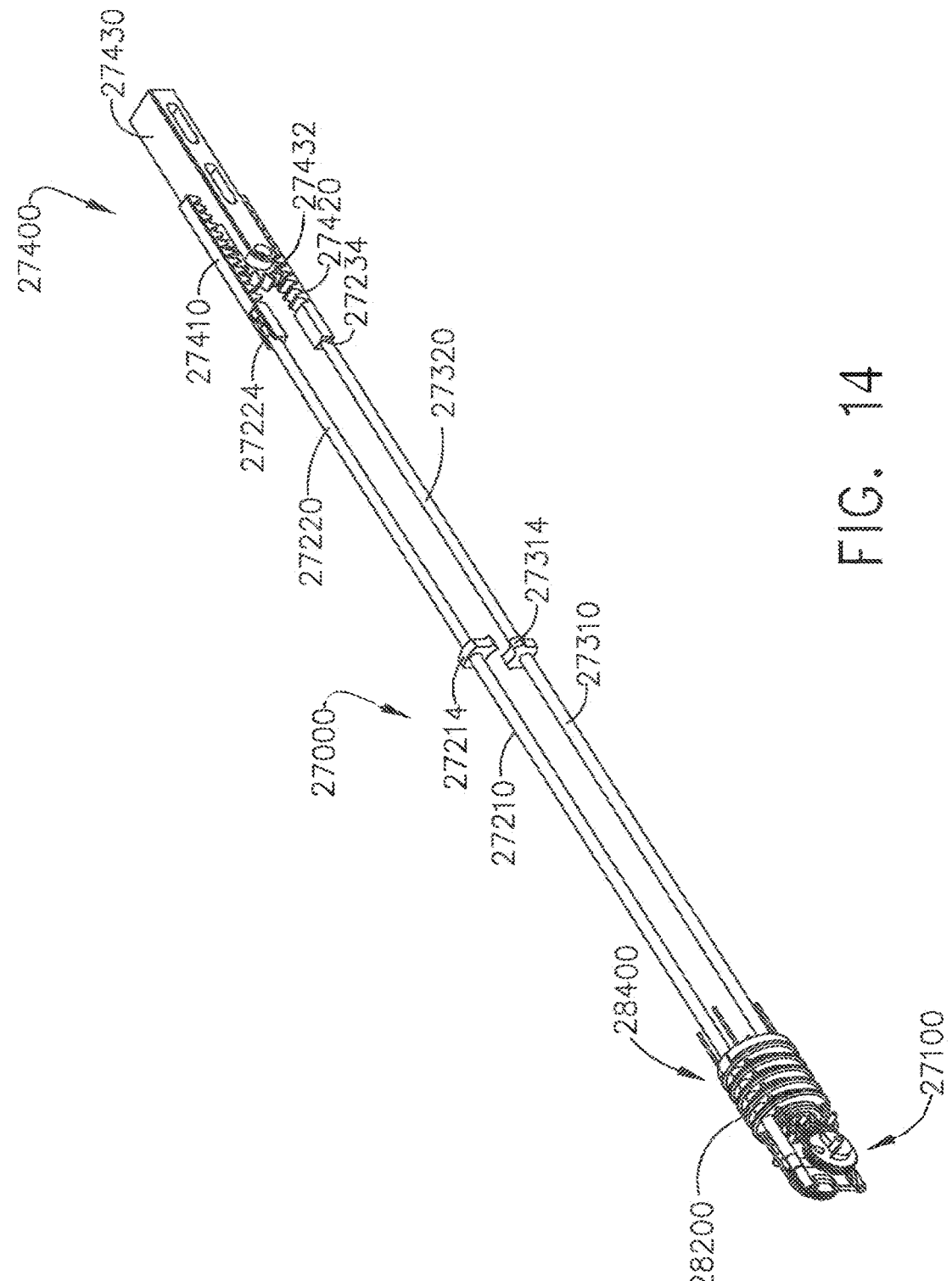
Figure 15:
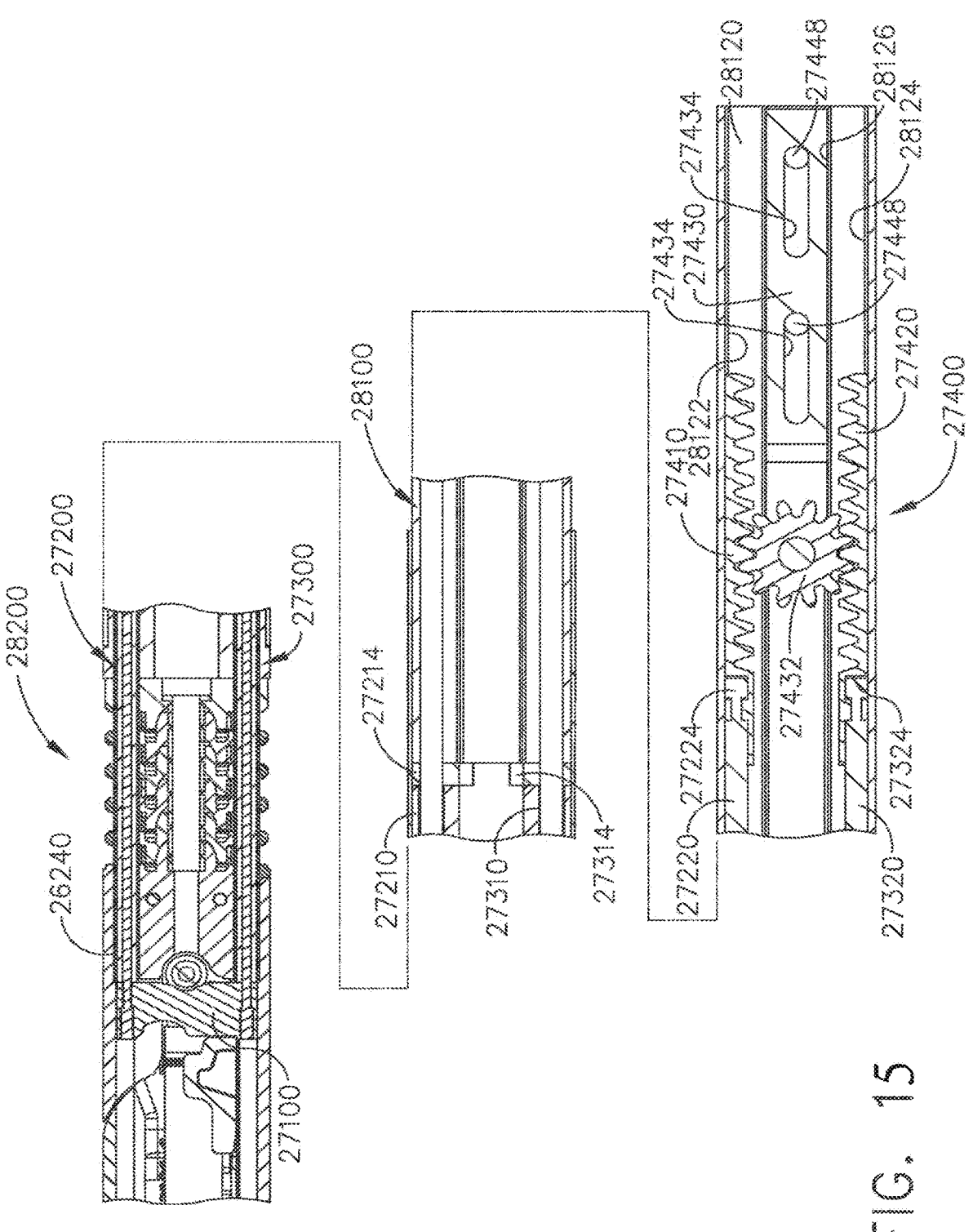
Figure 16:
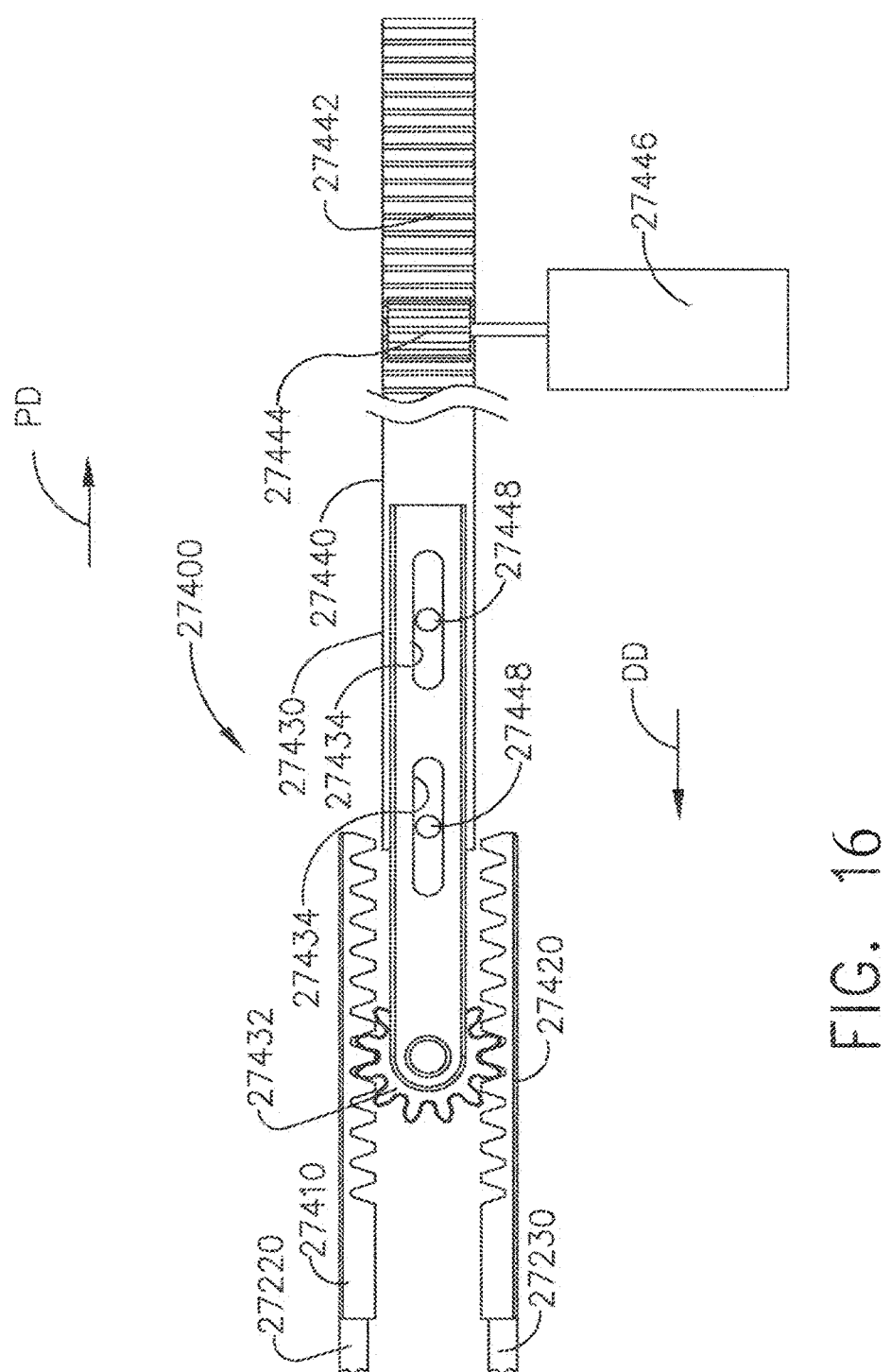
Figures 17, 18:
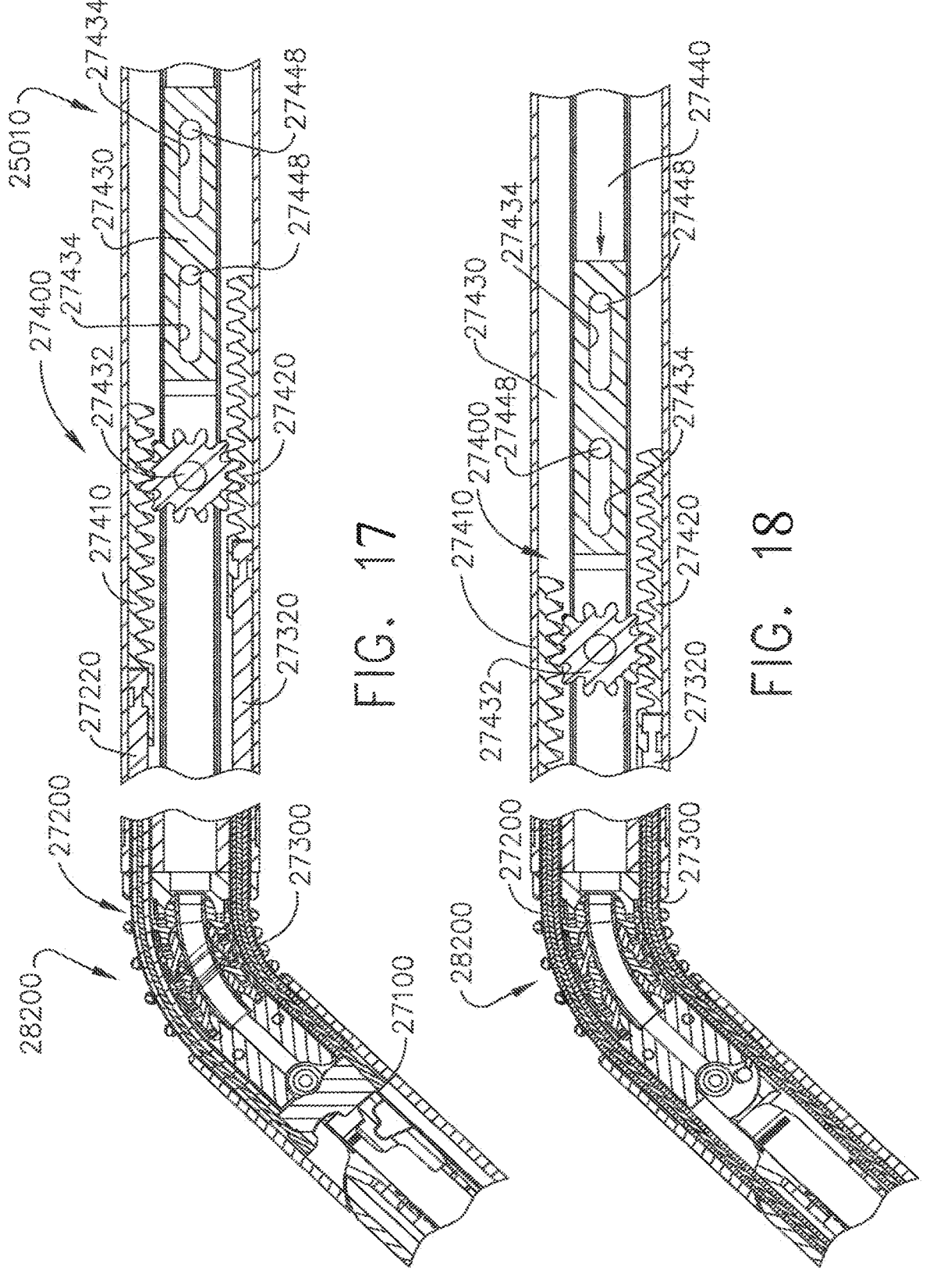
Figure 19A:
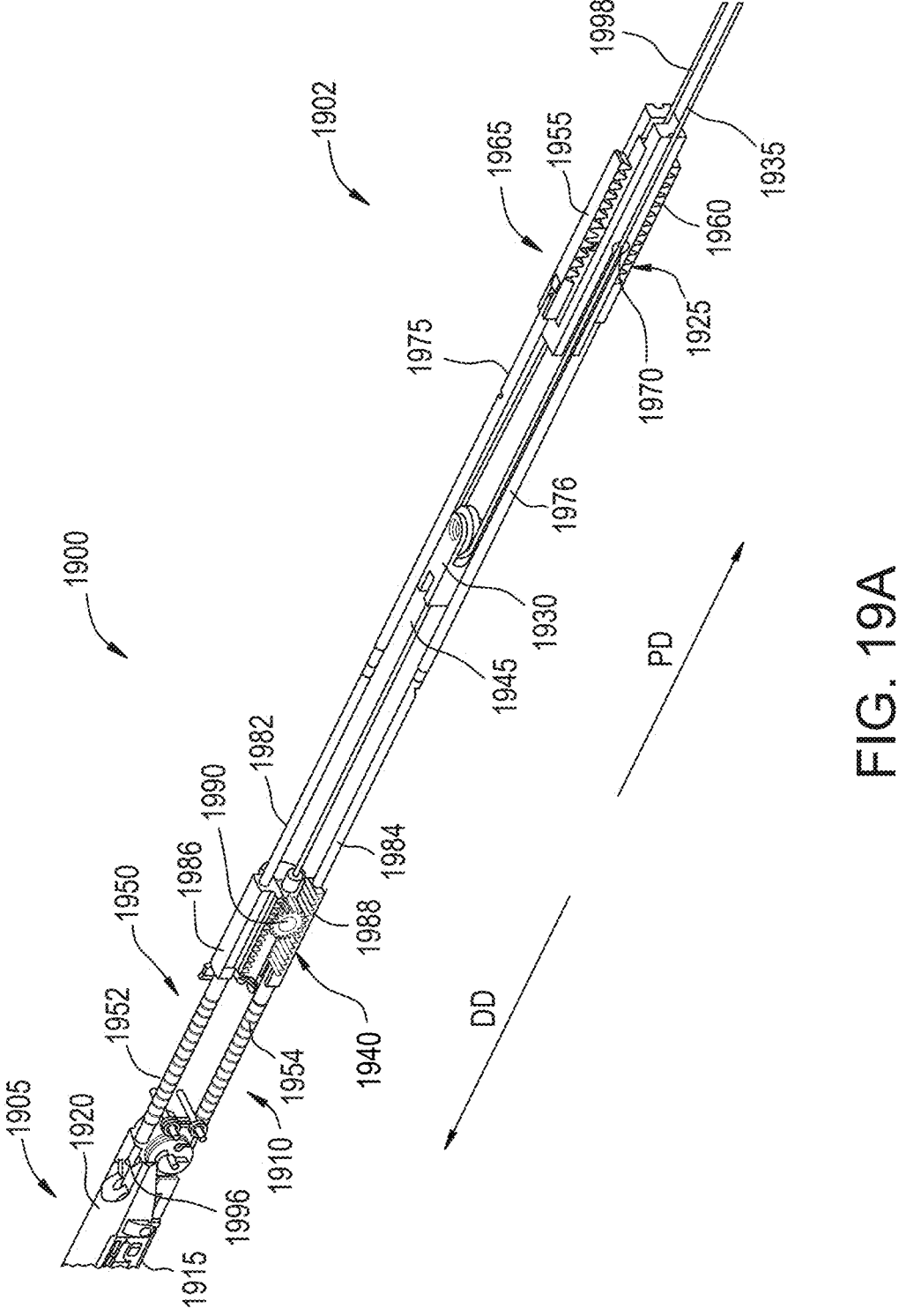
Figure 19B:
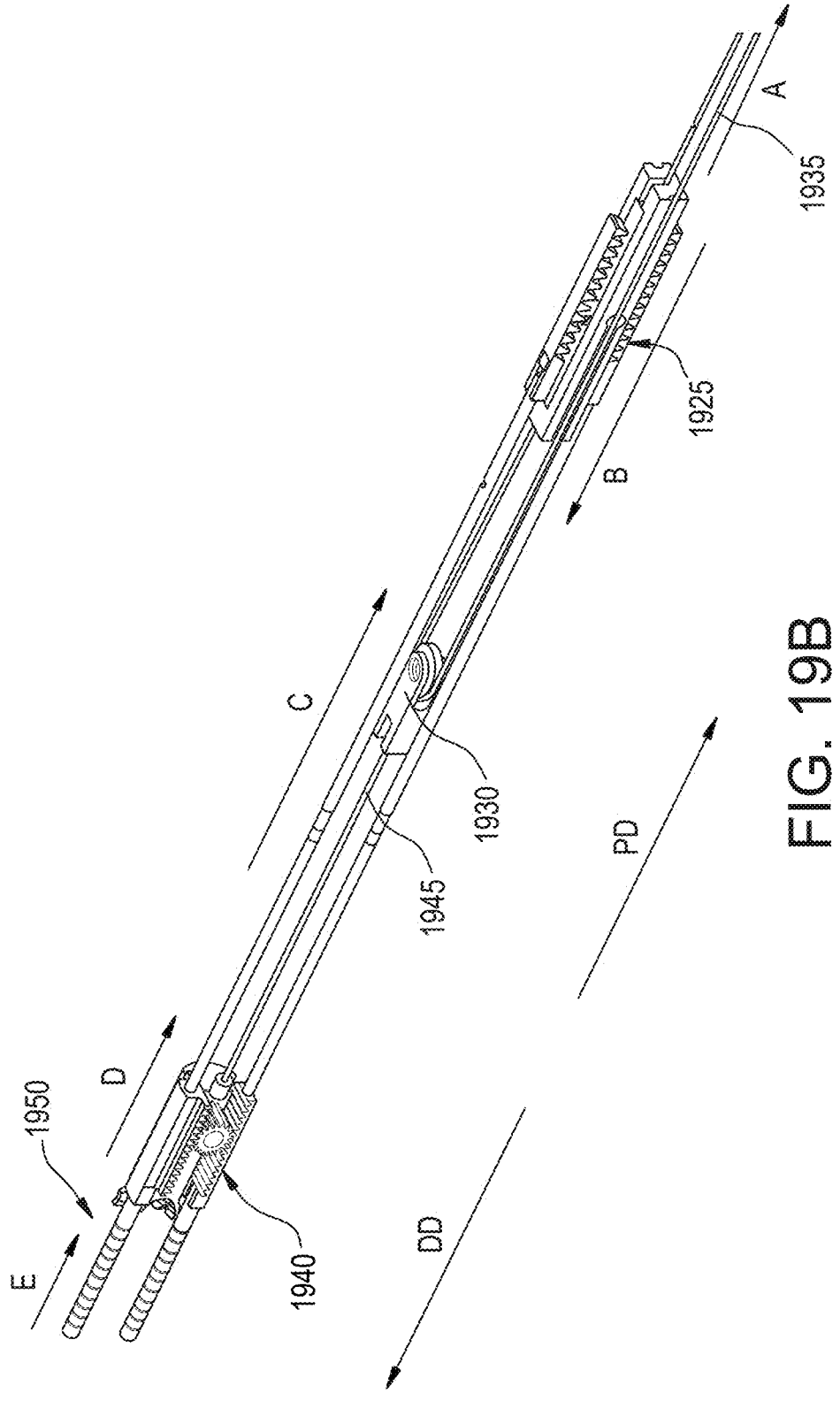
Figure 20:
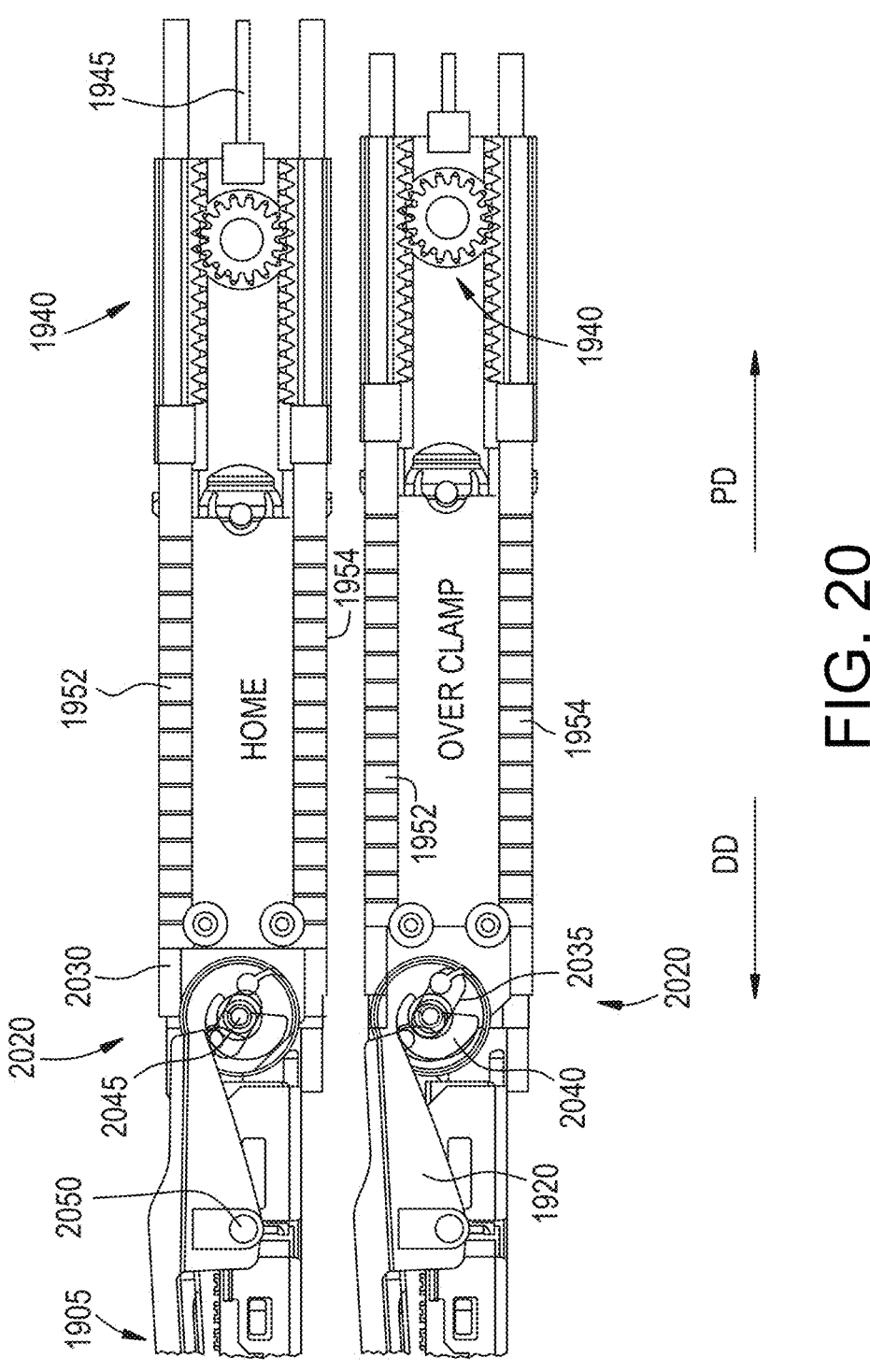
Figure 21:
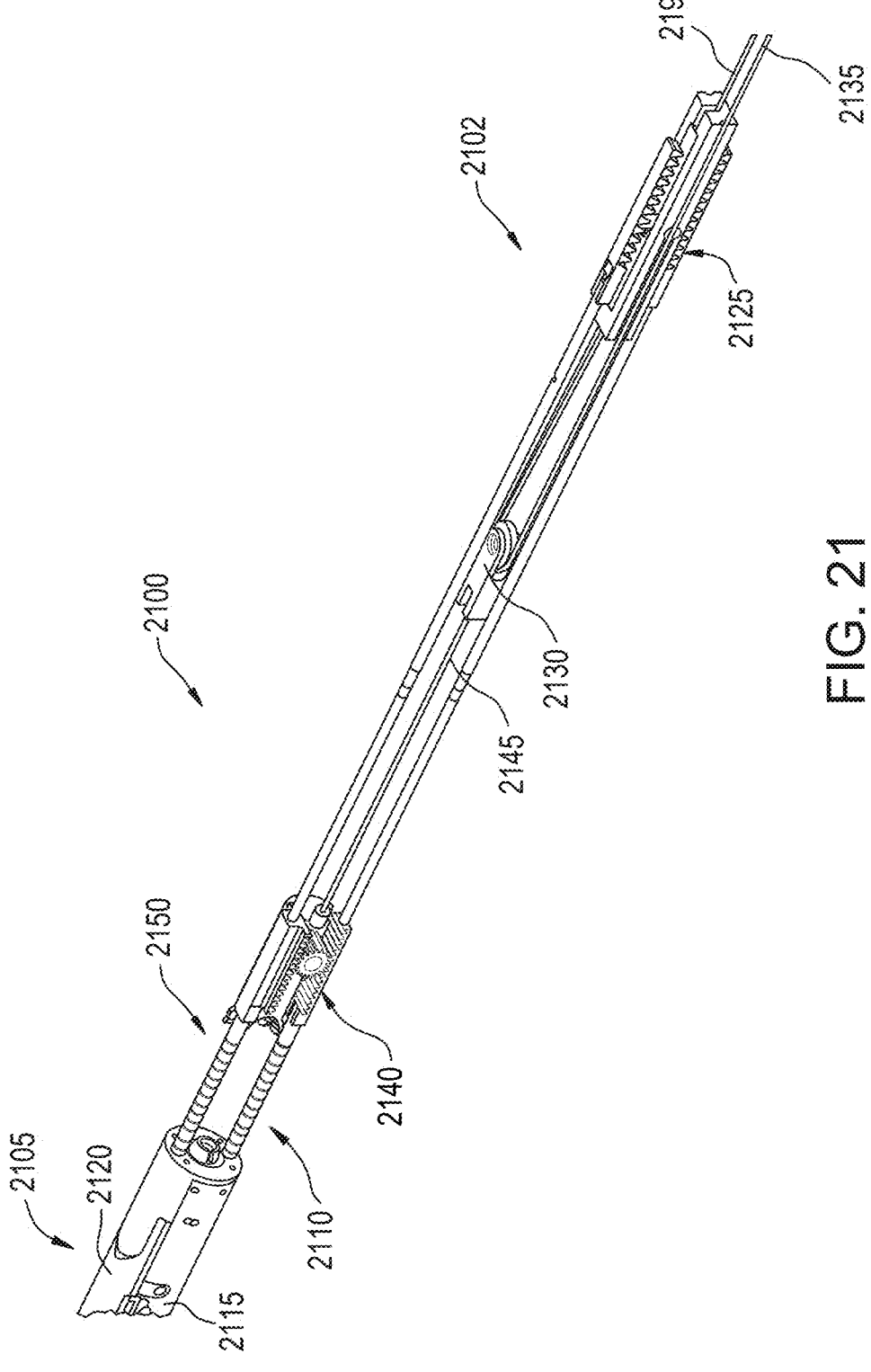
Figure 22:
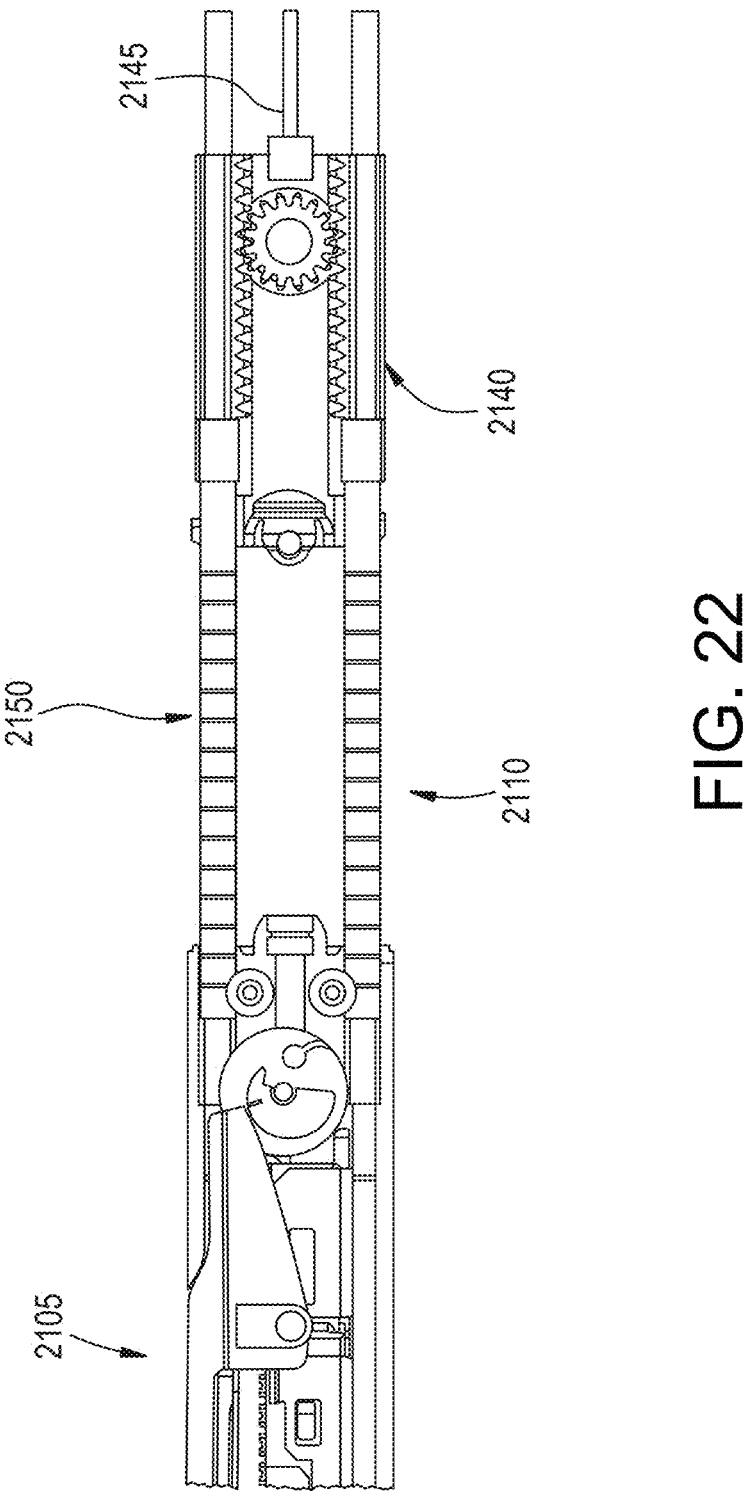
Figure 23:
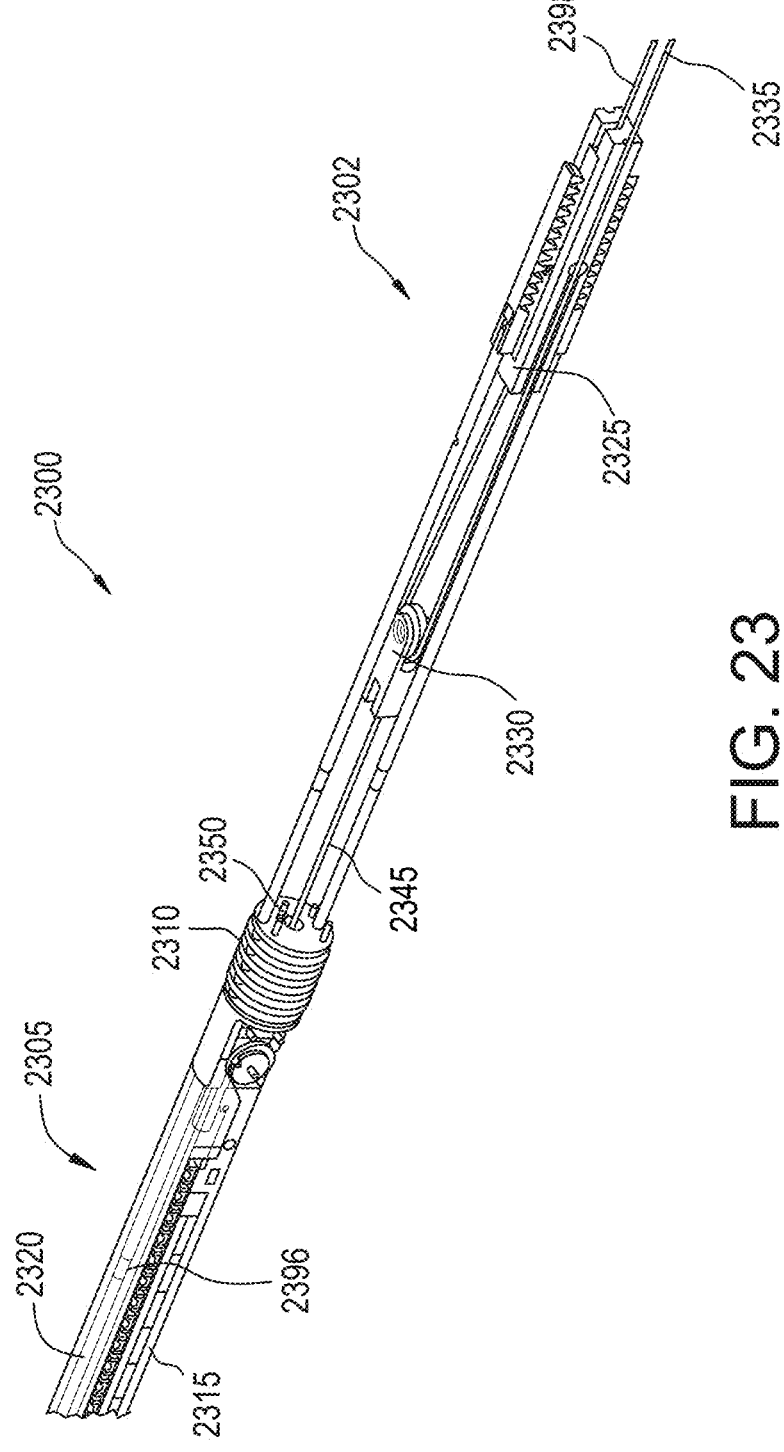
Figure 24:
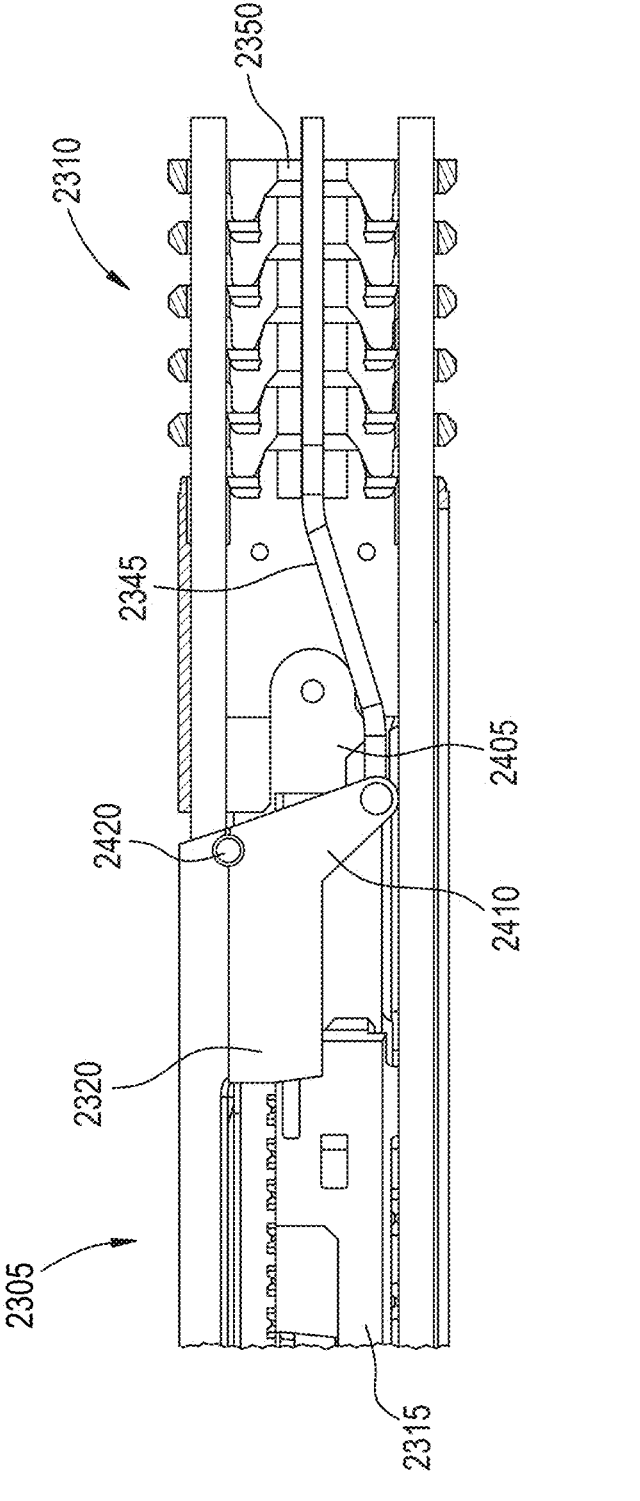
Figure 25:
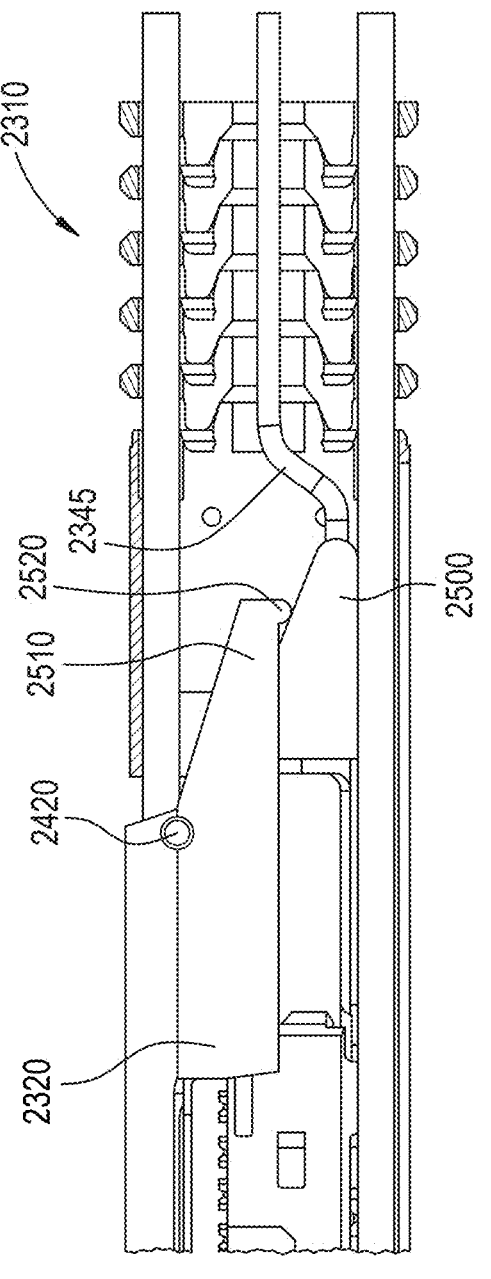
Figure 26:
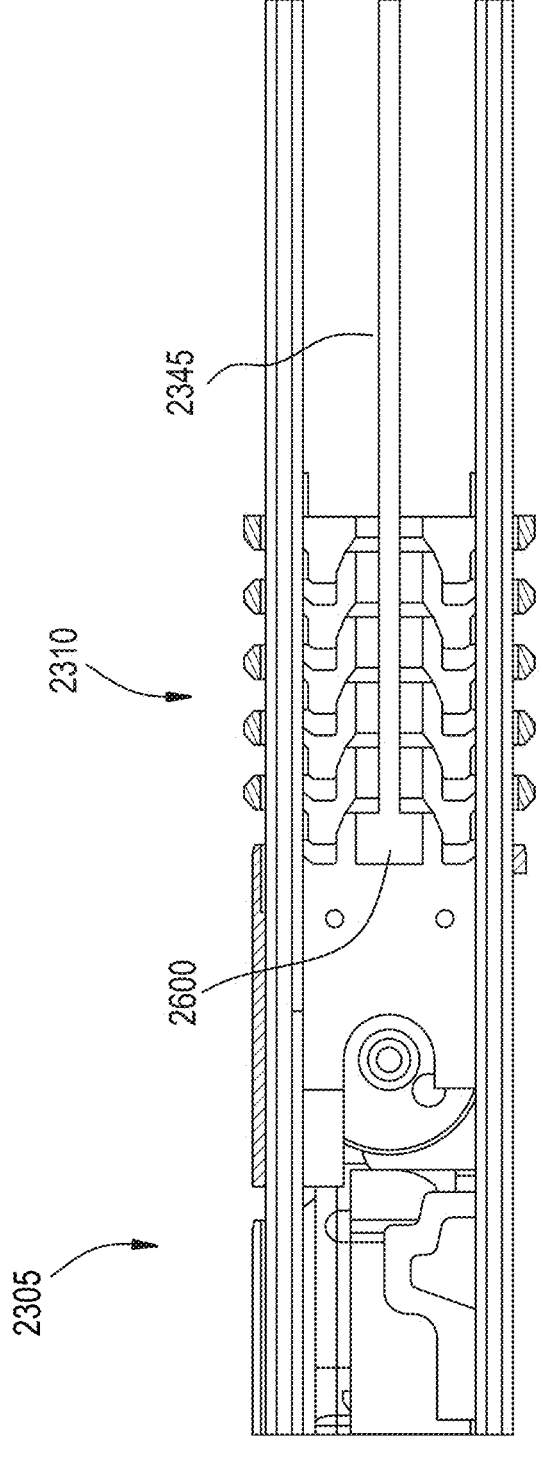
Figure 27:
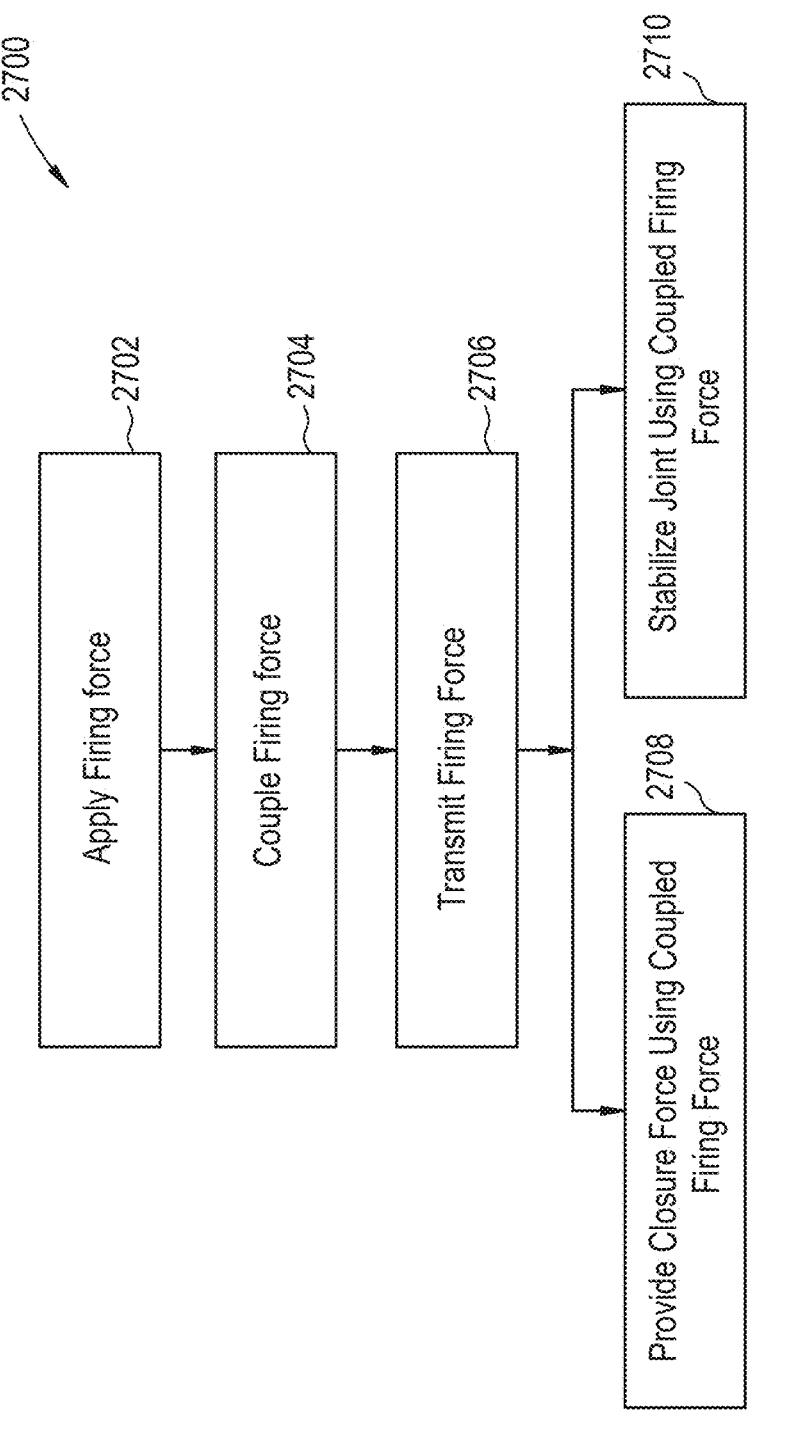

FIG. 11 is a view of a proximal face of the annular disc member of FIG. 8;

FIG. 12 is a perspective view of a portion of a firing system of the surgical instrument of FIG. 1;

FIG. 13 is a partial cross-sectional view of the firing system of FIG. 12;

FIG. 14 is a perspective view of the firing system, articulation joint, and a closure system of the surgical instrument of FIG. 1;

FIG. 15 is a partial cross-sectional view of the surgical instrument of FIG. 1 with the surgical end effector thereof in an unarticulated position;

FIG. 16 is a partial view of a differential drive assembly embodiment of the firing system of the surgical instrument of FIG. 1;

FIG. 17 is another partial cross-sectional view of the surgical instrument of FIG. 1 with the surgical end effector thereof in an articulated position;

FIG. 18 is another partial cross-sectional view of the surgical instrument of FIG. 1 with the surgical end effector thereof in an articulated position;

FIG. 19A depicts a perspective view of a firing redirect assembly according to one embodiment;

FIG. 19B depicts schematically the movement of the various components of the firing redirect assembly of FIG. 19A according to one embodiment;

FIG. 20 depicts side cross-sectional views of different states of a portion of the firing redirect assembly of FIG. 19A and a closure system according to one embodiment;

FIG. 21 depicts a perspective view of a firing redirect assembly according to another embodiment;

FIG. 22 depicts a side cross-sectional view of a portion of the firing redirect assembly of FIG. 21 according to one embodiment;

FIG. 23 depicts a perspective view of a firing redirect assembly according to another embodiment;

FIG. 24 depicts a side cross-sectional view of a portion of the firing redirect assembly of FIG. 23 according to one embodiment;

FIG. 25 depicts a side cross-sectional view of a portion of the firing redirect assembly of FIG. 23 according to another embodiment;

FIG. 26 depicts a side cross-sectional view of a portion of the firing redirect assembly of FIG. 23 according to another embodiment; and FIG. 27 is a flowchart of an example method of operating a surgical tool according to one embodiment.

The drawings are not intended to be limiting in any way, and it is contemplated that various embodiments of the technology disclosed herein may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those having ordinary skill in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the technology or inventive concepts described herein.

Recitation of ranges of values herein are not intended to be limiting, referring instead individually to any and all values falling within the range, unless otherwise indicated herein, and each separate value within such a range is incorporated into the disclosure as if it were individually recited herein. Furthermore, the terms "about," "approximately," "substantially," and the like as used herein in connection with any numerical values, ranges of values, and/or geometric/positional quantifications are intended to encompass the exact value(s) or quantification(s) referenced as well as a suitable tolerance that enables the referenced feature or combination of features to function for the intended purpose described herein. For example, "substantially parallel" encompasses nominally parallel structures.

References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or", etc.

As used herein in connection with various examples of end effector jaw tips, a tip described as "angled," "bent," or "curved" encompasses tip configurations in which a longitudinal path (e.g., linear or arcuate) along which the tip extends is non-coaxial and non-parallel with a longitudinal axis of the jaw body; particularly, configurations in which the longitudinal tip path extends distally toward the opposing jaw. Conversely, a tip described as "straight" encompasses tip configurations in which a longitudinal axis of the tip is substantially parallel or coaxial with the longitudinal axis of the jaw body.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

It is common practice during various laparoscopic surgical procedures to insert a surgical end effector portion of a surgical instrument through a trocar that has been installed in the abdominal wall of a patient to access a surgical site located inside the patient's abdomen. In its simplest form, a trocar is a pen-shaped instrument with a sharp triangular point at one end that is typically used inside a hollow tube, known as a cannula or sleeve, to create an opening into the body through which surgical end effectors may be introduced. Such arrangement forms an access port into the body cavity through which surgical end effectors may be inserted. The inner diameter of the trocar's cannula necessarily limits the size of the end effector and drive-supporting shaft of the surgical instrument that may be inserted through the trocar.

Regardless of the specific type of surgical procedure being performed, once the surgical end effector has been inserted into the patient through the trocar cannula, it is often necessary to move the surgical end effector relative to the shaft assembly that is positioned within the trocar cannula in order to properly position the surgical end effector relative to the tissue or organ to be treated. This movement or positioning of the surgical end effector relative to the portion of the shaft that remains within the trocar cannula is often referred to as "articulation" of the surgical end effector. A variety of articulation joints have been developed to attach a surgical end effector to an associated shaft in order to facilitate such articulation of the surgical end effector. As one might expect, in many surgical procedures, it is desirable to employ a surgical end effector that has as large a range of articulation as possible.

Due to the size constraints imposed by the size of the trocar cannula, the articulation joint components must be sized so as to be freely insertable through the trocar cannula. These size constraints also limit the size and composition of various drive members and components that operably interface with the motors and/or other control systems that are supported in a housing that may be handheld or comprise a portion of a larger automated system. In many instances, these drive members must operably pass through the articulation joint to be operably coupled to or operably interface with the surgical end effector. For example, one such drive member is commonly employed to apply articulation control motions to the surgical end effector. During use, the articulation drive member may be unactuated to position the surgical end effector in an unarticulated position to facilitate insertion of the surgical end effector through the trocar and then be actuated to articulate the surgical end effector to a desired position once the surgical end effector has entered the patient.

Thus, the aforementioned size constraints form many challenges to developing an articulation system that can effectuate a desired range of articulation, yet accommodate a variety of different drive systems that are necessary to operate various features of the surgical end effector. Further, once the surgical end effector has been positioned in a desired articulated position, the articulation system and articulation joint must be able to retain the surgical end effector in that locked position during the actuation of the end effector and completion of the surgical procedure. Such articulation joint arrangements must also be able to withstand external forces that are experienced by the end effector during use.

A variety of surgical end effectors exist that are configured to cut and staple tissue. Such surgical end effectors commonly include a first jaw feature that supports a surgical staple cartridge and a second jaw that comprises an anvil. The jaws are supported relative to each other such that they can move between an open position and a closed position to position and clamp target tissue therebetween. Many of these surgical end effectors employ an axially moving firing member. In some end effector designs, the firing member is configured to engage the first and second jaws such that as the firing member is initially advanced distally, the firing member moves the jaws to the closed position. Other end effector designs employ a separate closure system that is independent and distinct from the system that operates the firing member.

The staple cartridge includes a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities may be arranged in six longitudinal rows. Three rows of staple cavities may be positioned on a first side of a longitudinal slot and three rows of staple cavities may be positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, in these surgical end effectors, the sled is moved distally by the firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

Many surgical end effectors employ an axially movable firing beam that is attached to the firing member and is used to apply axial firing and retraction motions to the firing member. Many of such firing beams comprise a laminated construction that affords the firing beam with some degree of flexure about the articulation joint. As the firing beam traverses the articulation joint, the firing beam can apply de-articulation forces to the joint and can cause the beam to buckle. To prevent the firing beam from buckling under pressure, the articulation joint is commonly provided with lateral supports or "blow-out" plate features to support the portion of the beam that traverses the articulation joint. To advance the firing beam through an angle of greater than sixty degrees, for example, a lot of axial force is required. This axial force must be applied to the firing member in a balanced manner to avoid the firing member from binding with the jaws as the firing member moves distally. Any binding of the firing member with the jaws can lead to component damage and wear as well as require an increased amount of axial drive force to drive the firing member through the clamped tissue.

Other end effector designs employ a firing member that is rotary powered. In many of such designs, a rotary drive shaft extends through the articulation joint and interfaces with a rotatable firing member drive shaft that is rotatably supported within one of the jaws. The firing member threadably engages the rotatable firing member drive shaft and, as the rotatable firing member drive shaft is rotated, the firing member is driven through the end effector. Such arrangements require the supporting jaw to be larger to accommodate the firing member drive shaft. In such devices, a lower end of the firing member commonly operably interfaces with the drive shaft which can also result in an application of forces that tend to unbalance the firing member as it is driven distally.

Many surgical end effectors employ a firing member that is pushed distally through a surgical staple cartridge by an axially movable firing beam. The firing beam is commonly attached to the firing member in the center region of the firing member body. This attachment location can introduce an unbalance to the firing member as it is advanced through the end effector. Such unbalance can lead to undesirable friction between the firing member and the end effector jaws. The creation of this additional friction may require an application of a higher firing force to overcome such friction as well as can cause undesirable wear to portions of the jaws and/or the firing member. An application of higher firing forces to the firing beam may result in unwanted flexure in the firing beam as it traverses the articulation joint. Such additional flexure may cause the articulation joint to de-articulate—particularly when the surgical end effector is articulated at relatively high articulation angles.

In previous endocutter arrangements, the firing member is pushed by a flexible beam. In such arrangements, the articulation joint must redirect the linear motion of the flexible beam as it enters the articulation joint back to that linear motion as it exits the articulation joint and enters the end effector. Because of the high loads required to push the flexible beam and the firing member, the flexible beam commonly experiences high amounts of friction as it exits the articulation joint and is linearly redirected into the end effector. This added amount of friction increases the amount of driving forces that are required to drive the firing member from the starting to ending position within the end effector while the end effector is articulated. Further, as the flexible beam traverses the articulation joint, it may apply de-articulation motions to the articulation joint components. Thus, the articulation joint components must be sufficiently robust so as to resist such de-articulation motions.

Other forms of surgical endocutters employ rotary forces to drive the firing member through the end effector. Such arrangements commonly employ a rotary drive screw that is housed within the channel that supports the staple cartridge. During use, the sled and tissue place large moments on the firing member which decrease the efficiency of the system and ultimately require higher rotary forces to actuate the firing member. It is difficult to move the rotary drive screw closer to the center of such forces because of the cartridge and the location of the tissue. It is also difficult to package a screw on top and bottom of the firing member without increasing the overall diameter of the surgical end effector.

I. Illustrative Surgical Stapler

FIGS. 1-18 illustrate an example of surgical instrument 25010 that may address many of the challenges facing surgical instruments that comprise end effectors that are articulatable to large articulation angles and that are configured to cut and fasten tissue. In various embodiments, the surgical instrument 25010 may comprise a handheld device. In other embodiments, the surgical instrument 25010 may comprises an automated system sometimes referred to as a robotically-controlled system, for example. In various forms, the surgical instrument 25010 comprises a surgical end effector 26000 that is operably coupled to an elongate shaft assembly 28000. The elongate shaft assembly 28000 may be operable attached to a housing. In one embodiment, the housing may comprise a handle that is configured to be grasped, manipulated and actuated by the clinician. In other embodiments, the housing may comprise a portion of a robotic system that houses or otherwise operably supports at least one drive system that is configured to generate and apply at least one control motion which could be used to actuate the surgical end effectors disclosed herein and their respective equivalents. In addition, various components may be "housed" or contained in the housing or various components may be "associated with" a housing. In such instances, the components may not be contained with the housing or supported directly by the housing. For example, the surgical instruments disclosed herein may be employed with various robotic systems, instruments, components and methods disclosed in U.S. Pat. No. 9,072,535, entitled SURGICAL STAPLING INSTRUMENTS WITH ROTATABLE STAPLE DEPLOYMENT ARRANGEMENTS, which is incorporated by reference herein in its entirety.

Figure 5:
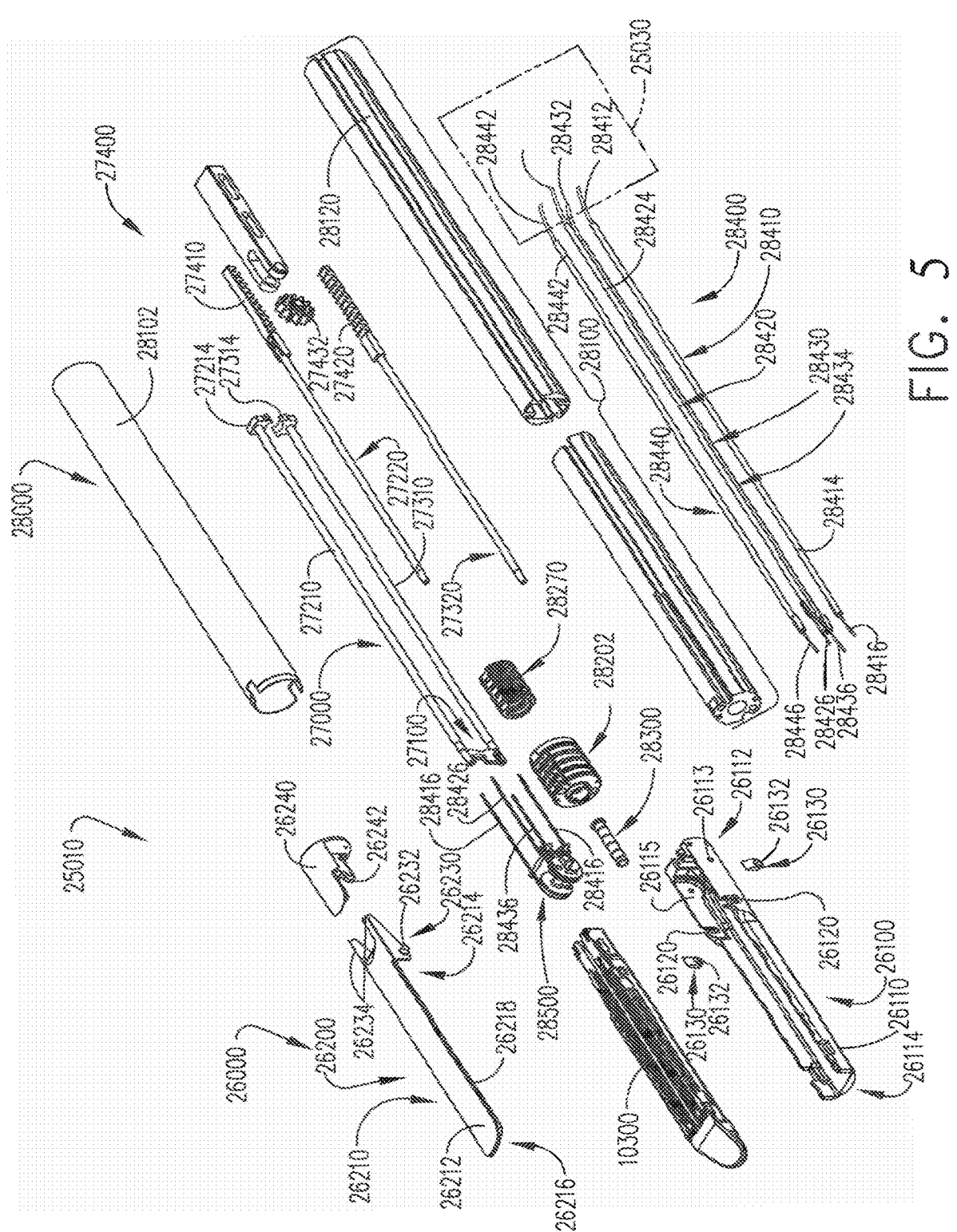
FIG. 5 is an exploded assembly perspective view of a portion of the surgical instrument of FIG. 1.

In one form, the surgical end effector 26000 comprises a first jaw 26100 and a second jaw 26200. In the illustrated arrangement, the first jaw 26100 comprises an elongate channel 26110 that comprises a proximal end 26112 and a distal end 26114 and is configured to operably support a surgical staple cartridge therein. An example of a surgical staple cartridge was described above. The second jaw 26200 comprises an anvil 26210 that comprises an elongate anvil body 26212 that has a proximal end 26214 and a distal end 26216. The anvil body 26212 comprises a staple-forming undersurface 26218 that faces the first jaw 26100 and may include a series of staple-forming pockets (not shown) that corresponds to each of the staples or fasteners in the surgical staple cartridge 10300. As can be seen in FIG. 5, the proximal end 26214 of the anvil body 26212 comprises an anvil mounting portion 26230 that comprises a pair of laterally extending mounting pins 26232 that are configured to be received in corresponding mounting inserts 26130 that are configured to be retainingly received within mounting cradles 26120 formed in a proximal end 26112 of the elongate channel 26110. The mounting pins 26232 are pivotally received within pivot holes 26132 in the mounting inserts 26130 and then the mounting inserts 26130 are inserted into their corresponding cradle 26120 and affixed to the elongate channel 26110 by welding, adhesive, snap fit, etc. Such arrangement facilitates pivotal travel of the anvil 26210 relative to the elongate channel 26110 about a fixed pivot axis PA. See FIG. 1. As stated above, as used in this context, the term "fixed" means that the pivot axis PA is non-translating or non-moving relative to the elongate channel 26110.

In the illustrated arrangement, the elongate shaft assembly 28000 defines a shaft axis SA and comprises a shaft spine assembly 28100 that is received in a hollow outer shaft tube 28102. See FIG. 5. The shaft spine assembly 28100 may operably interface with a housing of the control portion (e.g., handheld unit, robotic tool driver, etc.) of the surgical instrument 25010 and in one example, comprises a proximal spine segment 28120 and a distal spine segment 28140.

Figure 6:
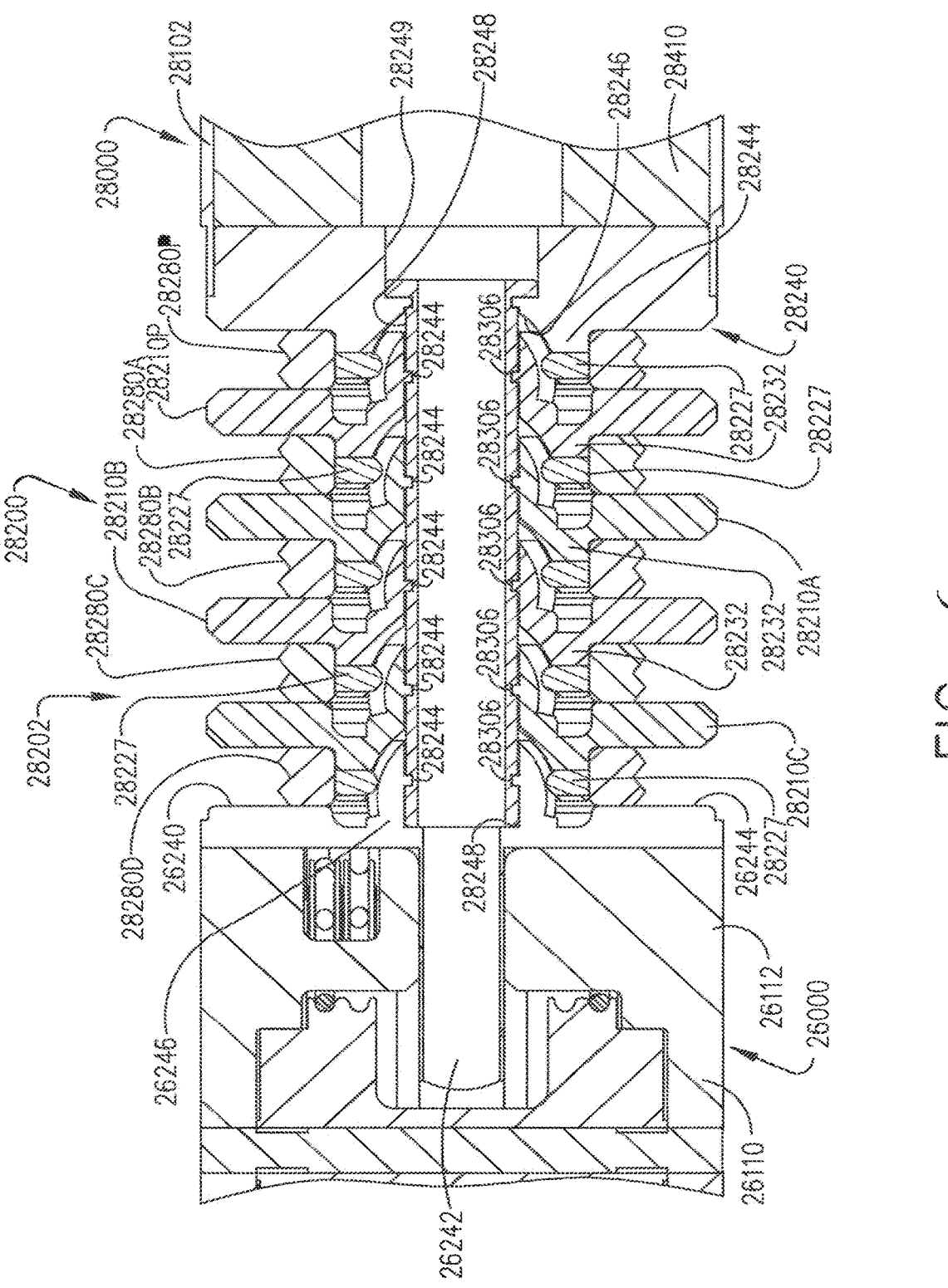
FIG. 6 is a bottom cross-sectional view of an articulation joint and portions of the anvil of the surgical instrument of FIG. 1.
Figure 7:
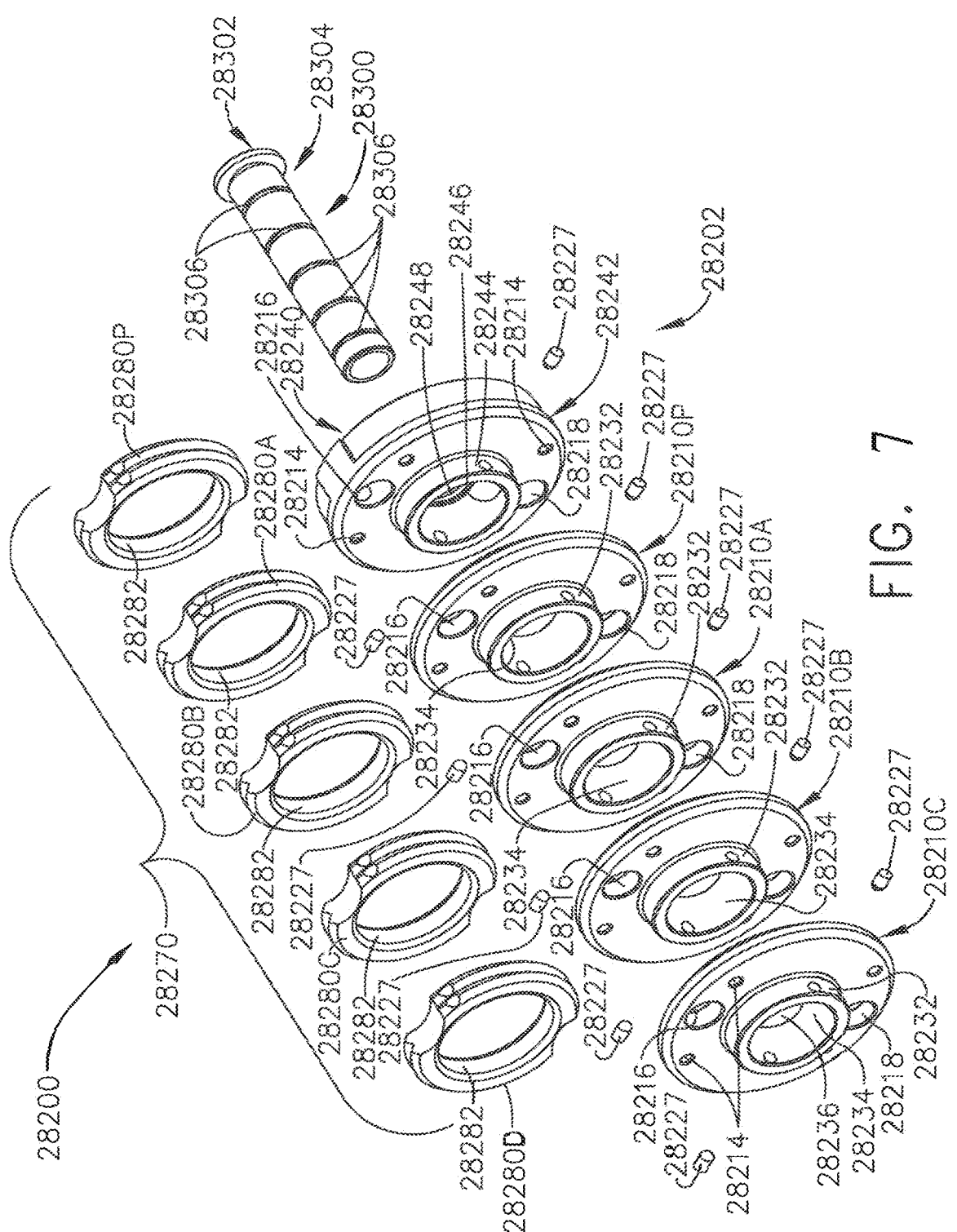
FIG. 7 is an exploded assembly view of the articulation joint of FIG. 6.

The elongate shaft assembly 28000 further comprises an articulation joint 28200 that may be attached to the distal spine segment 28140 as well as the surgical end effector 26000 to facilitate selective articulation of the surgical end effector 26000 relative to the elongate shaft assembly 28000 in multiple articulation planes. Turning now to FIGS. 6-11, the articulation joint 28200 comprises a series 28202 of movably interfacing annular disc members 28210. As can be seen in FIGS. 8, 9, and 11, each annular disc member 28210 comprises a "first" or proximal face 28220 that comprises a centrally-disposed spherical feature or protrusion 28222. Each annular disc member 28210 further comprises a second or distal face 28230 that comprises an annular hub portion 28232 that defines a concave socket 28234 therein. See FIGS. 8 and 10. Each annular disc member 28210 further has a central shaft passage 28236 therethrough. As can be seen in FIGS. 6 and 7, the articulation joint 28200 further comprises a proximal attachment disc assembly 28240 that is configured to be attached to a distal end of the distal spine segment 28140 by welding, adhesive, or other suitable fastener arrangement. The proximal attachment disc assembly 28240 comprises a distal face 28242 that includes an annular hub portion 28244 that defines a concave socket 28246 therein. The proximal attachment disc 28240 further has a central shaft passage 28248 therethrough. Also in the illustrated arrangement, the anvil mounting bracket 26240 is configured to operably interface with the articulation joint 28200. The anvil mounting bracket 26240 is attached to the proximal end 26112 of the elongate channel 26110 of the surgical end effector 26000 by welding, adhesive or other suitable fastener arrangements and comprises a proximal face 26244 that has a centrally-disposed spherical feature or protrusion 26246 protruding therefrom. See FIG. 6. The anvil mounting bracket 26240 further has a central shaft passage 26248 therethrough.

In at least one embodiment, the articulation joint further comprises a series 28270 of elastomeric annular spacer members 28280 that serve to space and provide elastic support between each annular disc member 28210. The elastomeric annular spacer members 28280 define a spacer opening 28282 such that each elastomeric annular spacer member 28280 may be journaled on an annular hub portion 28232 of a corresponding annular disc member 28210. Each annular disc member 28210 is journaled on a central elastomeric support or continuum shaft 28300 that is mounted to the proximal attachment disc assembly 28240 and the anvil mounting bracket 26240. In one arrangement, the central continuum shaft 28300 is fabricated from an elastomeric material (e.g., rubber, polymer, etc.) and comprises a flanged proximal end 28302 and a cylindrical body portion 28304. The cylindrical body portion 28304 comprises a series of annular grooves 28306 therein. Each annular groove 28306 corresponds to one of the annular disc members 28210. The annular disc members 28210 and annular spacer members 28280 are journaled on the central continuum shaft 28300 as shown in FIG. 6. The flanged proximal end 28302 of the central continuum shaft 28300 is supported in a proximal passage 28249 in the proximal attachment disc 28240. The cylindrical body portion 28304 of the central continuum shaft 28300 extends through the central passage 28236 in each of the annular disc members 28210 in the series 28202 of movably interfacing annular disc members 28210. Each centrally-disposed spherical feature or protrusion 28222 comprises an annular key member 28224 that is configured to be received in a corresponding annular groove 28306 in the central continuum shaft 28300. Such arrangement may serve to orient each annular disc member 28210 in a desired spacing orientation on the central continuum shaft 28300, for example.

Still referring to FIG. 6, a proximal-most elastomeric spacer member 28280P is journaled on the annular hub portion 28244 of the proximal attachment disc assembly 28240 such that it is positioned between a proximal-most annular disc member 28210P and the proximal attachment disc 28240. The annular key member 28224 of the proximal-most annular disc member 28210P is received within a corresponding annular groove 28306 in the central continuum shaft 28300 to position the centrally-disposed spherical feature or protrusion 28222 of the proximal-most annular disc member 28210P within the concave socket 28246 in the annular hub portion 28244 of the proximal attachment disc 28240. As can further be seen in FIG. 6, another elastomeric spacer member 28280A is journaled on the annular hub portion 28232 of the proximal-most annular disc member 28210P such that is positioned between the next annular disc member 28210A in the series 28202 of movably interfacing annular disc members 28202 and the proximal-most annular disc member 28210P. The annular key member 28224 of the annular disc member 28210A is received within a corresponding annular groove 28306 in the central continuum shaft 28300 to position the centrally-disposed spherical feature or protrusion 28222 of the annular disc member 28210A within the concave socket 28246 in the annular hub portion 28244 of the proximal attachment disc 28210P. Still referring to FIG. 6, another elastomeric spacer member 28280B is journaled on the annular hub portion 28232 of the annular disc member 28210A such that is positioned between the next annular disc member 28210B in the series 28202 of movably interfacing annular disc members 28210. The annular key member 28224 of the annular disc member 28210B is received within a corresponding annular groove 28306 in the central continuum shaft 28300 to position the centrally-disposed spherical feature or protrusion 28222 of the annular disc member 28210B within the concave socket 28246 in the annular hub portion 28244 of the annular disc member 28210A. Also in this arrangement, another elastomeric spacer member 28280C is journaled on the annular hub portion 28232 of the annular disc member 28210B such that is positioned between the distal-most annular disc member 28210C in the series of movably interfacing annular disc members 28202. The annular key member 28224 of the distal-most annular disc member 28210C is received within a corresponding annular groove 28306 in the central continuum shaft 28300 to position the centrally-disposed spherical feature or protrusion 28222 of the distal-most annular disc member 28210C within the concave socket 28246 in the annular hub portion 28244 of the annular disc member 28210B. Finally, another elastomeric spacer member 28280D is journaled on the annular hub portion 28232 of the distal-most annular disc member 28210C such that is positioned between the anvil mounting bracket 26240 and the distal-most annular disc member 28210C. The annular key member 28224 of the centrally-disposed spherical feature or protrusion 26246 of the anvil mounting bracket 26240 is received within a corresponding annular groove 28306 in the central continuum shaft 28300 to position the centrally-disposed spherical feature or protrusion 226246 of the anvil mounting bracket 26240 within the concave socket 28246 in the annular hub portion 28244 of the distal-most annular disc member 28210C.

In at least one arrangement, to limit pivotal travel of the annular disc members to a range of relative pivotal travel and prevent complete relative rotation of the annular disc members 28210 relative to each other, the centrally-disposed spherical feature or protrusion 28222 of each of the annular disc member 28210P, 28210A, 28210B, 28210C, as well as the distal spherical feature or protrusion 26246 of the anvil mounting bracket 26240, includes a pair of arcuate pin grooves 28226 therein. As can be seen in FIG. 6, a corresponding travel-limiting pin member 28227 is pressed into or otherwise attached to each annular hub portion 28232 and is received within the corresponding pin groove 28226 in the centrally-disposed spherical feature or protrusions 28222, 26246.

Returning to FIG. 5, in the illustrated example, the articulation joint 28200 may be operably controlled by an articulation system 28400 that comprises four cable assemblies 28410, 28420, 28430, and 28440 that extend through the elongate shaft assembly 28000. In one arrangement, the cable assembly 28410 comprises a proximal cable portion 28412 that is attached to an articulation rod 28414 that is supported in a corresponding axial groove in the shaft spine assembly 28100 for axial travel therein. A distal cable portion 28416 is attached to the articulation rod 28414. The cable assembly 28420 comprises a proximal cable portion 28422 that is attached to an articulation rod 28424 that is supported in a corresponding axial groove in the shaft spine assembly 28100 for axial travel therein. A distal cable portion 28426 is attached to the articulation rod 28414. The cable assembly 28430 comprises a proximal cable portion 28432 that is attached to an articulation rod 28434 that is supported in a corresponding axial groove in the shaft spine assembly 28100 for axial travel therein. A distal cable portion 28436 is attached to the articulation rod 28434. The cable assembly 28440 comprises a proximal cable portion 28442 that is attached to an articulation rod 28444 that is supported in a corresponding axial groove in the shaft spine assembly 28100 for axial travel therein. A distal cable portion 28446 is attached to the articulation rod 28444.

The proximal cable portions 28412, 28422, 28432, 28442 may operably interface with a portion of a cable control system 25030 that is supported within or is otherwise associated with a housing of the surgical instrument 25010. The cable control system 25030 may comprise a plurality of cable support members/capstans, pulleys, etc. that are controlled by one or more corresponding motors that are controlled by a control circuit portion of the surgical instrument 25010. In various embodiments, the cable control system

25030 is configured to manage the tensioning (pulling) and paying out of cables at precise times during the articulation process. In addition, in at least one arrangement, the cable control system 25030 may be employed to control the opening and closing of the anvil 26210, as disclosed in U.S. Pat. No. 11,883,024, entitled METHOD OF OPERATING A SURGICAL INSTRUMENT, which is incorporated by reference herein in its entirety.

Referring now to FIGS. 12 and 13, in at least one embodiment, the firing system 27000 comprises a firing member 27100 that includes a vertically-extending firing member body 27112 that comprises a top firing member feature 27120 and a bottom firing member feature 27130. A tissue cutting blade 27114 is attached to or formed in the vertically-extending firing member body 27112. In at least one arrangement, the top firing member feature 27120 comprises a top tubular body 27122 that has a top axial passage 27124 extending therethrough.

See FIG. 13. The bottom firing member feature 27130 comprises a bottom tubular body 27132 that has a bottom axial passage 27134 extending therethrough. In at least one arrangement, the top firing member feature 27120 and the bottom firing member feature 27130 are integrally formed with the vertically-extending firing member body 27112. In at least one example, the anvil body 26212 comprises an axially extending anvil slot that has a cross-sectional shape that resembles a "keyhole" to accommodate passage of the top firing member feature 27120 in the various manners discussed herein. Similarly, the elongate channel 26110 comprises an axially extending channel slot that also has a keyhole cross-sectional shape for accommodating passage of the bottom firing member feature 27130 as described above.

In the illustrated arrangement, the firing system 27000 comprises an upper firing assembly 27200 that operably interfaces with the top firing member feature 27120. The upper firing assembly 27200 includes an upper flexible outer tube or conduit 27210 that has a proximal end 27212 that is fixed to an upper insert 27214 that is non-movably attached to the shaft spine assembly 28100. For example, the upper insert 27214 may be welded to the shaft spine assembly 28100 or otherwise be attached thereto by adhesive or other appropriate fastening means. The flexible outer tube or conduit 27210 extends through upper passages 28216 provided through the proximal attachment disc assembly 28240, the proximal-most annular disc member 28210P, the annular disc members 28210A, 28210B, 28210C and the anvil mounting bracket 26240. A distal end 27216 of the flexible outer tube or conduit 27210 may be affixed to the anvil mounting bracket 26240.

In the illustrated embodiment, the upper firing assembly 27200 further includes an upper push rod 27220 that is slidably supported in a corresponding axial passage in the shaft spine assembly 28100. The upper firing assembly 27200 further comprises an upper push coil 27230 that is supported in an inner flexible upper sleeve 27240 which extends through the upper flexible outer tube or conduit 27210. A proximal end 27232 of the upper push coil 27230 and a proximal end 27242 of the inner flexible upper sleeve 27240 abut a distal end 27222 of the upper push rod 27220. The upper push coil 27230 is hollow and may comprise a coil spring that is fabricated from Nitinol, titanium, stainless steel, etc. In other arrangements, the upper push coil 27230 comprises a laser cut "hypotube" that essentially comprises a hollow tubular member with offset laser cuts therein which enable the hypotube to flex and bend while being capable of transmitting axial forces or motions. The inner flexible upper sleeve 27240 may be fabricated from a polymer or similar material and prevent tissue, fluid, and/or debris from infiltrating into the upper push coil 27230 which may hamper its ability to flex and bend during articulation of the surgical end effector relative to the elongate shaft assembly.

As can be seen in FIG. 13, a distal end 27234 of the upper push coil 27230 as well as a distal end 27244 of the inner flexible upper sleeve 27240 abut a proximal end 27123 of the top tubular body 27122 or the top firing member feature 27120. Also in the illustrated arrangement, the upper firing assembly further comprises an upper push coil cable 27250 that extends through the hollow upper push coil 27230. The upper push coil cable 27250 comprises an upper cable proximal end 27252 that is secured to the distal end 27222 of the upper push rod 27220 and an upper cable distal end 27254 that is secured within the top axial passage 27124 in the top tubular body 27122 of the top firing member feature 27120 by an upper attachment lug 27256. The upper push coil cable 27250 is held in tension between the top firing member feature 27120 an the upper push rod 27220 which serves to retain the distal end 27234 of the upper push coil 27230 as well as a distal end 27244 of the inner flexible upper sleeve 27240 in abutting contact with the proximal end 27123 of the top tubular body 27122 of the top firing member feature 27120 and the proximal end 27232 of the upper push coil 27230 and a proximal end 27242 of the inner flexible upper sleeve 27240 in abutting contact with the distal end 27222 of the upper push rod 27220.

In the illustrated example, the firing system 27000 further comprises a lower firing assembly 27300 that operably interfaces with the bottom firing member feature 27130. The lower firing assembly 27300 includes a lower flexible outer tube or conduit 27310 that has a proximal end 27312 that is fixed to a lower insert 27314 that is non-movably attached to the shaft spine assembly 28100. For example, the lower insert 27314 may be welded to the shaft spine assembly 28100 or otherwise be attached thereto by adhesive or other appropriate fastening means. The lower flexible outer tube or conduit 27310 extends through lower passages 28218 provided in each of the proximal attachment disc assembly 28240, the proximal-most annular disc member 28210P, annular disc members 28210A, 28210B, 28210C and anvil mounting bracket 26240. A distal end 27316 of the flexible outer tube or conduit 27310 is affixed to the anvil mounting bracket 26240.

In the illustrated embodiment, the lower firing assembly 27300 further includes a lower push rod 27320 that is slidably supported in a corresponding axial passage in the shaft spine assembly 28100. The lower firing assembly 27300 further comprises a lower push coil 27330 that is supported in an inner flexible lower sleeve 27340 which extends through the lower flexible outer tube or conduit 27310. A proximal end 27332 of the lower push coil 27330 and a proximal end 27342 of the inner flexible lower sleeve 27340 abut a distal end 27322 of the lower push rod 27320. The lower push coil 27330 is hollow and may comprise a coil spring that is fabricated from Nitinol, titanium, stainless steel, etc. In other arrangements, the lower push coil 27330 comprises a laser cut hypotube that essentially comprises a hollow tubular member with offset laser cuts therein which enable the hypotube to flex and bend. The inner flexible lower sleeve 27340 may be fabricated from a polymer or similar material and prevent tissue, fluid, and/or debris from infiltrating into the lower push coil 27330 which may hamper its ability to flex during articulation.

As can be seen in FIG. 13, a distal end 27334 of the lower push coil 27330 as well as a distal end 27344 of the inner flexible lower sleeve 27340 abut a proximal end 27133 of the bottom tubular body 27132 of the bottom firing member feature 27130. Also in the illustrated arrangement, the lower firing assembly 27300 further comprises a lower push coil cable 27350 that extends through the hollow lower push coil 27330. The lower push coil cable 27350 comprises a lower cable proximal end 27352 that is secured to the distal end 27322 of the lower push rod 27320 and a lower cable distal end 27354 that is secured within the bottom axial passage 27134 in the bottom tubular body 27132 of the bottom firing member feature 27130 by a lower attachment lug 27356. The lower push coil cable 27350 is held in tension between the bottom firing member feature 27130 an the lower push rod 27320 which serves to retain the distal end 27334 of the lower push coil 27330 as well as a distal end 27344 of the inner flexible lower sleeve 27340 in abutting contact with the proximal end 27133 of the bottom tubular body 27132 of the bottom firing member feature 27130 and the proximal end 27332 of the lower push coil 27330 and a proximal end 27342 of the inner flexible lower sleeve 27340 in abutting contact with the distal end 27322 of the lower push rod 27320.

In the illustrated arrangement, the firing system 27000 further comprises a differential drive assembly 27400 that is configured to axially drive the upper firing assembly 27200 and the lower firing assembly 27300. Turning to FIGS. 15-18, in at least one arrangement, a proximal end 27224 of the upper push rod 27220 is coupled to a first or upper gear rack 27410 of the differential drive assembly 27400. As can be seen in FIG. 15, the first or upper gear rack 27410 is slidably supported in an upper proximal axial cavity 28122 in the proximal spine segment 28120. Similarly, a proximal end 27324 of the lower push rod 27320 is coupled to a second or lower gear rack 27420 that is supported for axial travel within a lower proximal axial cavity 28124 in the proximal spine segment 28120. The differential drive assembly 27400 further comprises an axially movable carrier member 27430 that is centrally disposed between the first or upper gear rack 27410 and the second or lower gear rack 27420 and is supported for axial travel within a proximal axial cavity 28126 in the proximal spine segment 28120. See FIG. 15. Still referring to FIGS. 15-18, a pinion gear 27432 is pivotally pinned to the axially movable carrier member 27430 such that the pinion gear 27432 is meshing engagement with the first or upper gear rack 27410 and the second or lower gear rack 27420. The axially movable carrier member 27430 is driven axially within the proximal axial cavity 28126 in the proximal spine segment 28120 by a firing drive actuator 27440. See FIG. 16. In one arrangement, the firing drive actuator 27440 comprises a firing drive gear rack 27442 that drivingly interfaces with a drive gear 27444 that is driven by a firing motor 27446 that may be operably supported in or otherwise associated with the housing of the surgical instrument 25010. In other arrangements, the firing drive actuator 27440 may be axially driven distally and proximally by a cylinder arrangement or other suitable actuator interfacing therewith. As can be seen in FIGS. 16-18, the firing drive actuator 27440 may be attached to the axially movable carrier member 27430 by a pair of spaced coupler pins 27448 that are attached to the firing drive actuator 27440 and are received within corresponding axial slots 27434 in the axially movable carrier member 27430. Such arrangement permits some relative axial movement between the firing drive actuator 27440 and the axially movable carrier member 27430. For example, when the firing drive actuator 27440 is driven distally in the distal direction DD, the axially movable carrier member 27430 will not move distally until the coupler pins 27448 reach the distal ends of their corresponding axial slots 27434 at which point the axially movable carrier member 27430 will move distally. Likewise, the when the firing drive actuator 27440 is driven in the proximal direction PD, the axially movable carrier member 27430 will not move proximally until the coupler pins 27448 reach the proximal ends of their corresponding axial slots 27434 at which point the axially movable carrier member 27430 will move proximally.

Surgical stapling devices need to apply a high force on the firing member over a long displacement to form the staples and cut tissue. Transmitting that force through an articulated joint is especially challenging because it is difficult to redirect the forces in the desired direction and withstand the loads applied to it. The differential drive assembly 27400 described herein addresses and solves many, if not all of such challenges by employing two flexible outer tubes or conduits 27210, 27310 to constrain the paths of the flexible push coils 27230, 27330, respectively. As described herein, the upper flexible outer tube or conduit 27210 surrounds a portion of the upper push coil 27230 and the upper flexible outer tube or conduit 27310 surrounds a portion of the lower push coil 27330. Each of the outer tubes or conduits 27210, 27310 can bend but they also can resolve an axial tensile load. The ability to bend allows for the firing member force to be redirected through the articulated joint, and the ability to resolve tension allows for it to change the direction in which the push coil goes. When the push coil 27230, 27330 is put in compression, the flexible outer tube or conduit 27210, 27310 is put in tension. The outer tubes or conduits 27210, 27310 prevent the push coils 27230, 27330 from buckling. The outer tubes 27210, 27310 are terminated in a manner to resolve the tensile loads. As described above, the distal end 27216 of the flexible outer tube or conduit 27210 and the distal end 27316 of the flexible outer tube or conduit 27310 are both affixed to the anvil mounting bracket 26240. The proximal end 27212 of the flexible outer tube or conduit 27210 and the proximal end 27312 of the flexible outer tube or conduit 27310 are both affixed to the shaft spine assembly 28100. The pinion gear 27432 is in meshing engagement with the first or upper gear rack 27410 and the second or lower gear rack 27420 such that when one of the racks 27410, 27420 moves in one axial direction, the other rack 27410, 27420 axially moves in an opposite direction. As can be seen in FIGS. 17 and 18, during articulation, the pinion gear 27432 rotates so the flexible outer tubes or conduits 27210, 27310 can move to account for the change in path length. However, when the firing drive actuator 27440 is driven in the distal direction DD, the axially movable carrier member 27430 is actuated to push the push coils 27230, 27330 distally through the outer tubes or conduits 27210, 27310 to fire (i.e., drive the firing member 27100 distally) the tensile loads in the two flexible outer tubes or conduits 27210, 27310 react against one another without any motion of the pinion gear 27432.

In accordance with one general aspect, the upper passages 28216 form an upper pathway 28221 (FIG. 3) through the articulation joint 28200. Similarly, the lower passages 28218 form a lower pathway 28223 through the articulation joint 28200. When the surgical end effector 26000 is in an unarticulated position (i.e., the surgical end effector is axially aligned with the elongate shaft assembly 28000 on the shaft axis SA-FIGS. 1, 3, 4), the upper pathway 28221 and the lower pathway 28223 are parallel to each other. See FIG. 3. When the surgical end effector 26000 is in an articulated position relative to the elongate shaft assembly 28000, the upper pathway 28221 and the lower pathway 28223 are concentric to each other. See FIG. 2.

When the surgical end effector 26000 is in the unarticulated position, the firing system 27000 may be actuated to drive the firing member 27100 from a starting position within the proximal end 26112 of the elongate channel 26100 to an ending position within the distal end 26114 of the elongate channel 26110. When the surgical end effector 26000 is in the unarticulated position, and the firing system 27000 is actuated, the differential drive assembly 27400 drives the upper firing assembly 27200 and the lower firing assembly 27300 equal axial distances in a same axial direction (i.e., the distal direction DD) to apply an upper axial drive motion and a lower axial drive motion to the firing member 27100. The upper axial drive motion and the lower axial drive motion are substantially equal in magnitude which serves to distally advance the firing member 27100 through the surgical end effector 26000 without binding which might otherwise occur should the upper axial drive motion and the lower axial drive motions be different in magnitude. Similarly, when the surgical end effector 26000 is in an articulated position relative to the elongate shaft assembly 28000, the firing system 27000 may be actuated to drive the firing member 27100 from the starting position to the ending position. In such instances, the differential drive assembly 27400 is configured to permit the upper firing assembly 27200 and the lower firing assembly 27300 to move in substantially equal distances in opposite axial directions to accommodate the articulated position. The differential drive assembly 27400 may then apply an upper axial drive motion and a lower axial drive motion that are equal to each other to the firing member 27100. For example, depending upon the articulated position of the surgical end effector 26000 relative to the elongate shaft assembly 28000, the upper firing assembly 27200, upon articulation of the surgical end effector 26000, may be moved proximally a first distance and the lower firing assembly 27300 may be positioned relative thereto distally a second distance that is substantially equal to the first distance by the pinion gear 27432. Thereafter, distal actuation of the firing drive actuator 27440 will cause the upper firing assembly 27200 and the lower firing assembly 27300 to apply an upper axial drive motion and a lower axial drive motion that are equal to each other to the firing member 27100. As used herein, when the carrier is moved distally, the carrier may apply "axial control motions" to the upper firing assembly 27200 and the lower firing assembly 27300. Thus, when the surgical end effector 26000 is in an unarticulated configuration, the carrier may apply equal amounts of axial control motions to the upper firing member 27200 and the lower firing member 27300 in the same axial direction (distal direction DD) and when the surgical end effector 26000 is in an articulated configuration, the carrier may apply "other equal amounts" of axial control motions to the upper firing member 27200 and the lower firing member 27300 in the same axial direction (distal direction DD) to move the firing member 27100 from the starting position to the ending position.

II. Firing Coupled Closure and Joint Reaction

In general, the highest firing forces established in an endocutter are associated with cutting and stapling tissue. As indicated above, when the knife encounters thicker tissue, the knife must do the additional work of compressing the tissue, which generates high loads on the knife translation subsystem, such as the firing system 27000 described above. If the same high firing forces can be used to help close the anvil, then the additional loads on the firing system can be minimized. Therefore, it is desired to reduce the force to fire the knife by increasing the closure load on the anvil. The disclosed embodiments couple the force to fire the firing member, or knife, with the closure force of closing the anvil, which creates a mechanical feedback that increases the closure load as the knife encounters higher resistance. Thus, a force proportional to the firing force is provided to the closure system. Also, a high force displacement is provided to the distal side of the joint without any additional motor inputs. In this way, the disclosed embodiments capture waste energy, which improves the efficiency of the systems and components of the disclosed surgical instruments.

Also as indicated above, endocutters may also use a push firing system, which transmits the firing load directly through the articulation joint. As the firing load increases, the articulation joint reacts to the increased force. However, the reaction to the increased firing loads may negatively impact joint performance during normal operation and lead to problems, such as de-articulation. Therefore, it is desired for articulation joints of surgical staplers to react to the firing loads during firing without negatively impacting joint performance during normal operation. The disclosed embodiments couple the force to fire with the force holding the joint together, which creates a mechanical feedback that increases the joint tension as the knife encounters higher resistance. Thus, a force proportional to the firing force is provided to react to the firing loads through the joint. This also allows for additional joint retention forces not to be present during normal operation and therefore the additional joint retention forces do not impart additional resistance, friction, drag, etc.

The disclosed systems, devices, and methods involve a surgical tool, such as a surgical stapler, utilizing a firing system having upper and lower push rods and coils coupled to a knife at distal ends thereof and being pushed by a carrier system at proximal ends thereof, and a firing redirect assembly (or redirect firing subsystem) that redirects, or couples, increased firing loads to jaw closure and joint stabilization systems to assist with closing jaws to reduce the force to fire and to assist with stabilizing the articulation joint. The disclosed firing redirect assembly features a pulley and cable system, where a pulley couples a firing cable that receives firing loads to a reaction cable that uses a portion of the firing load for jaw closure and joint compression. As the firing cable is pulled proximally to advance the carrier system and thus the knife distally, the pulley and reaction cable coupled thereto are also pulled proximally. The reaction cable being pulled proximally not only causes additional closure rotation of the anvil in a number of possible ways, but also causes additional compression of the articulation joint.

The disclosed firing redirect assembly utilizes the increased firing loads to increase the closure load on the anvil, which allows the force to fire to be reduced. In this way, energy is redistributed, or "captured," and used to improve the efficiency of firing and closure systems. Increased efficiency allows for components to be made smaller and/or less complex, which allows for extra space for additional components and improved manufacturing capabilities. This redistribution of energy also allows for increased joint stabilization, which improves the performance of the joint during operation. The disclosed firing redirect assembly may be entirely enclosed within existing architecture of surgical staplers, such as those discussed above.

In particular, the disclosed embodiments relate to a firing redirect assembly for a surgical tool, including a firing carrier, a reaction pulley disposed distally from the firing carrier, and a firing cable coupled to a distal end of the firing carrier and wrapping around the reaction pulley and extending proximally past the firing carrier. The firing redirect assembly also includes a reaction cable coupled to and extending between a distal end of the reaction pulley and a proximal end of an end effector of the surgical tool, the end effector including a cartridge jaw and an anvil jaw pivotably connected to the cartridge jaw at a pivot. A firing load on the firing cable in a proximal direction causes the firing carrier to translate distally and causes the reaction pulley and the reaction cable to translate proximally, thereby assisting with closing the anvil jaw or assisting with stabilizing an articulation joint of the end effector.

FIG. 19A depicts a perspective view of a firing redirect assembly according to one embodiment. In one embodiment, the firing redirect assembly 1900 is configured to be used with a surgical tool, such as surgical instrument 25010 described above, having an elongate shaft, such as elongate shaft 28000 described above, an end effector 1905, such as end effector 26000 described above, and an articulation joint 1910, such as articulation joint 28200 described above. In another embodiment, the end effector 1905 may be different than the end effector 26000 described above and the articulation joint 1910 may be different than the articulation joint 28200 described above. For example, the articulation joint 1910 may include a flexible outer sleeve that houses the internal components of the joint 1910 as opposed to the series 28202 of movably interfacing annular disc members 28210 of the joint 28200 described above. The end effector 1905 is arranged at a distal end of the elongate shaft and includes opposing first 1915 and second 1920 jaws, such as first jaw 26100 and second jaw 26200 described above. The articulation joint 1910 interposes the end effector 1905 and the elongate shaft.

In one embodiment, the firing redirect assembly 1900 includes a firing carrier 1925, a reaction pulley 1930, a firing cable 1935, a floating redirect differential 1940, a reaction cable 1945, and one or more redirect tubes 1950. Together, these components redirect a portion of a firing force load applied to the firing cable 1935. That redirected firing force may be used to assist with closing the opposing first 1915 and second 1920 jaws, thereby reducing the required force to fire the surgical tool. The redirected firing force may also be used to compress, and thus stabilize, the articulation joint 1910 to minimize buckling and de-articulation. In another embodiment, the firing redirect assembly 1900 may include just the reaction pulley 1930, the floating redirect differential 1940, the reaction cable 1945, and the one or more redirect tubes 1950. In yet another embodiment, the firing redirect assembly 1900 may include just the reaction pulley 1930 and the reaction cable 1945.

In an embodiment, the firing carrier 1925 may be the same or similar as the axially movable carrier member 27430 described above, and part of a firing system 1902 somewhat similar to the firing system 27000 described above. In other words, the firing carrier 1925 may be an axially movable firing carrier 1925 that is centrally disposed between a first or upper gear rack 1955 and a second or lower gear rack 1960 of a differential drive assembly 1965, similar to the first or upper gear rack 27410 and the second or lower gear rack 27420 of the differential drive assembly 27400 described above. The firing carrier 1925 is supported for axial travel within a proximal axial cavity in a proximal spine segment, similar to the carrier member 27430 described above. See FIG. 15 and accompanying text. A pinion gear 1970, like pinion gear 27432 described above, is pivotally pinned to the firing carrier 1925 such that the pinion gear 1970 is in meshing engagement with the first or upper gear rack 1955 and the second or lower gear rack 1960. The firing carrier 1925 is driven axially within the proximal axial cavity in the proximal spine segment by a firing force, except rather than being driven in the distal direction (DD) by a direct push firing system as the firing system 27000 described above, the firing system 1902 implemented with the firing carrier 1925 of FIG. 19A involves an actuator/motor/drive system upstream in the proximal direction (PD) that exerts a pulling force on the firing cable 1935, which, as described below, results in the firing carrier 1925 moving distally. Operation of the firing system 1902 and the firing redirect assembly 1900 is described below.

In the embodiment shown in FIG. 19A, the firing system 1902 includes the firing cable 1935, the reaction pulley 1930, the firing carrier 1925, an upper 1975 and lower 1976 push rod extending distally from the firing carrier 1925, an upper 1982 and lower 1984 push coil coupled to and extending distally from the upper 1975 and lower 1976 push rods, respectively, and the knife body 1996. The one or more redirect tubes 1950 include an upper 1952 and lower 1954 redirect tube, and the upper 1982 and lower 1984 push coils extend distally through upper and lower portions of the redirect differential 1940 into the upper 1952 and lower 1954 redirect tubes, respectively. Distal ends of the upper 1982 and lower 1984 push coils are coupled to an upper and lower portion of the knife body 1996, respectively. The reaction pulley 1930 is disposed distally from the firing carrier 1925 and the firing cable 1935 is coupled to a distal end of the firing carrier 1925 and wraps around the reaction pulley 1930 and extends proximally past the firing carrier 1925 within the elongate shaft. A firing load on the firing cable 1935 in the proximal direction (PD) causes the firing carrier 1925 to move distally because of the firing cable 1935 being routed through the reaction pulley 1930. In this way, the firing system 1902 is similar to, and acts like, a block and tackle system. Movement of the firing carrier 1925 distally causes the upper 1975 and lower 1976 push rods, the upper 1982 and lower 1984 push coils, and the knife body 1996 to translate distally as well.

The firing system 1902 also includes a retract cable 1998 extending proximally from the firing carrier 1925, such that a pulling force on the retract cable 1998 by the upstream actuator causes the firing carrier 1925 to move proximally, which also causes the upper 1975 and lower 1976 push rods, the upper 1982 and lower 1984 push coils, and the knife body 1996 to translate proximally as well.

In one embodiment, the upper 1975 and lower 1976 push rods may be the same as or similar to the upper push rod 27220 and lower push rod 27320, respectively, described above. Similarly, the upper 1982 and lower 1984 push coils may be the same as or similar to the upper push coil 27230 and lower push coil 27330, respectively, described above. The surrounding and intervening components and architecture, as well as the operation, of the push rods 1975, 1976 and coils 1982, 1984 of FIG. 19A may be the same as that described above with reference to FIGS. 12-15. Note, however, that while some of the surrounding components and architecture of FIGS. 12-15 have been omitted for clarity, the description above of the components and architecture, and operation thereof, remains similar to that described herein.

As shown in FIG. 19A, the redirect differential 1940 is disposed distally from the reaction pulley 1930 and proximally from the articulation joint 1910. The redirect differential 1940 includes an upper gear rack 1986, a lower gear rack 1988, and a pinion gear 1990 in meshing engagement with the upper gear rack 1986 and the lower gear rack 1988, such that when one of the upper gear rack 1986 or lower gear rack 1988 moves in one axial direction, the other of the upper gear rack 1986 or lower gear rack 1988 axially moves in an opposite direction. The redirect differential 1940 operates similar to how the differential drive assembly 1965 operates, such that the pinion gear 1990 rotates to account for a change in path lengths of upper push coil 1982 and lower push coil 1984. The upper gear rack 1986 accommodates the upper push coil 1982 and the lower gear rack 1988 accommodates the lower push coil 1984. In other words, the upper gear rack 1986 and lower gear rack 1988 each include an axial passage extending between a proximal and distal end of the respective gear rack and the upper and lower push coils 1982, 1984 extend through the axial passages of the upper and lower gear racks 1986, 1988, respectively. During articulation of the articulation joint 1910, the pinion gear 1990 rotates causing the upper gear rack 1986 and lower gear rack 1988 to translate in opposite directions, thereby compensating for a change in path lengths of the upper push coil 1982 and lower push coil 1984, respectively.

The reaction cable 1945 is coupled to and extends between a distal end of the reaction pulley 1930 and a proximal end of the redirect differential 1940, as shown in FIG. 19A. Both the reaction cable 1945 and the firing cable 1935 may be flexible, rigid, or semi-rigid cables made of, for example, tungsten, spring steel, stainless steel, Nitinol, titanium, etc. In some examples, the reaction cable 1945 may be more rigid than the firing cable 1935, since the required bend radius of the reaction cable 1945 may be significantly less than the required bend radius of the firing cable 1935. In other words, since the firing cable 1935 needs to be able to bend around and through the reaction pulley 1930, the firing cable 1935 has a higher flexibility requirement than the reaction cable 1945. As described above, since the reaction cable 1945 couples the reaction pulley 1930 to the redirect differential 194, as the reaction pulley 1930 is pulled in the proximal direction, so too is the redirect differential 194 by way of the reaction cable 1945.

Still referring to FIG. 19A, the one or more redirect tubes 1950 are coupled to and extend between a distal end of the redirect differential 1940 and a proximal end of the end effector 1905. More particularly, a proximal end of the upper redirect tube 152 is coupled to a distal end of the upper gear rack 1986 of the redirect differential 1940. Likewise, a proximal end of the lower redirect tube 1954 is coupled to a distal end of the lower gear rack 1988 of the redirect differential 1940. Further, distal ends of the upper redirect tube 1952 and lower redirect tube 1954 are coupled to a proximal end of the end effector 1905. More particularly, distal ends of the upper redirect tube 1952 and lower redirect tube 1954 are coupled to a proximal end of a closure system of the end effector 1905, as described below with reference to FIG. 20.

As stated above, pushing a firing member, such as the knife body 1996, forward in an articulating end effector generally requires a lot of force and that force must be balanced. For example, when firing the knife body 1996 at an angle of greater than sixty degrees, it becomes very difficult to push a beam or rod or coil through the articulation joint 1910. The articulation joint 1910 also experiences significant loads which may cause the articulation joint 1910 to de-articulate. By employing upper and lower redirect tubes 1952, 1954 that are each flexible through the articulation joint 1910, but also rigid when put under tensile or compression forces, balanced loads may be applied to the push coils 1982, 1984 that are constrained to the push coils 1982, 1984 and not to the articulation joint 1910.

The upper and lower redirect tubes 1952, 1954 may be hollow flexible tension tubes or tensile members that include an axial passage extending therethrough to accommodate the upper and lower push coils 1982, 1984, respectively. In this way, the upper redirect tube 1952 surrounds a portion of the upper push coil 1982 and the lower redirect tube 1954 surrounds a portion of the lower push coil 1984. Each of the upper and lower redirect tubes 1952, 1954 can bend but they also can resolve an axial tensile load. The ability to bend allows for the firing force to be redirected through the articulated joint 1910, and the ability to resolve tension allows for it to change the direction in which the push coils 1982, 1984 move. When the push coils 1982, 1984 are put in compression (by the firing carrier 1925 moving distally), the upper and lower redirect tubes 1952, 1954 are put in tension (by being pulled proximally by the reaction pulley 1930 and reaction cable 1945). The upper and lower redirect tubes 1952, 1954 prevent the push coils 1982, 1984 from buckling. In other words, compression through the push coils 1982, 1984 in the center and balancing the tension of the redirect tubes 1952, 1954 on the outside keeps these components stable within the articulation joint 1910. The design and configuration of the redirect tubes 1952, 1954 also provide additional load bearing members that run through the articulation joint 1910.

In one example, the upper and lower redirect tubes 1952, 1954 may be laser cut hypotubes (described above) and/or may be made of a woven polymer or woven metal mesh or sheath.

The upper and lower push coils 1982, 1984 extend through the upper and lower redirect tubes 1952, 1954 and distal ends of the upper 1982 and lower 1984 push coils are coupled to an upper and lower portion of the knife body 1996, respectively. As the knife body 1996, which may be the same as or similar to the firing member 27100 described above, is advanced distally by the firing force, the knife body 1996 may encounter thicker tissue. When this happens, it becomes more difficult for the knife body 1996 to advance, since the knife body 1996 also helps compress the tissue by way of the top portion of the knife body 1996 advancing distally within a groove or channel of the anvil. In other words, the top portion of the knife body 1996 in the anvil helps keep the anvil closed while the knife body 1996 is fired, but when the knife body 1996 encounters thick tissue, greater loads are generated. Therefore, additional firing force and higher loads are placed on the firing system 1902, which can lead to operating issues, such as joint de-articulation and/or device failure. Thus, there is a need to redirect at least a portion of that extra generated force to both assist with closing the jaws and stabilizing the joint.

FIG. 19B depicts schematically the movement of the various components of the firing redirect assembly of FIG. 19A according to one embodiment. As shown in FIG. 19B, the firing redirect assembly 1900 of the present disclosure operates in conjunction with the firing system 1902. A firing load, depicted in FIG. 19B as arrow A, on the firing cable 1935 in a proximal direction imparted by an actuator/motor/drive system causes the firing carrier 1925 to translate distally, as shown by arrow B, which pushes the push rods 1975, 1976 and coils 1982, 1984 and knife body 1996 distally as well. In tandem with this action, the firing load on the firing cable 1935 in the proximal direction causes the reaction pulley 1930 to translate proximally, as shown by arrow C, since the firing cable 1935 is routed through the reaction pulley 1930 and pulling on the firing cable 1935 results in pulling the reaction pulley 1930. Since the reaction cable 1945 is coupled to the reaction pulley 1930, the reaction cable 1945 also translates (i.e., is pulled) in the proximal direction, also shown by arrow C. Since the redirect differential 1940 is coupled to the reaction cable 1945, as the reaction cable 1945 moves proximally, so too does the redirect differential 1940, as shown by arrow D. Similarly, since the one or more redirect tubes 1950 are coupled to the redirect differential 1940, the redirect differential 1940 translating proximally causes the one or more redirect tubes 1950 to translate proximally as well, as shown by arrow E. The movement described above exerts a proximally directed force on whatever the one or more redirect tubes 1950 are coupled to at the distal end, which may assist, impart, or induce either a closing force for closing the opposing first 1915 and second 1920 jaws or a tensile force for stabilizing the articulation joint 1910, as described below.

FIG. 20 depicts side cross-sectional views of different states of a portion of the firing redirect assembly 1900 of FIG. 19A and a closure system 2020 according to one embodiment. As shown in FIG. 20, the end effector 1905 includes a closure system 2020 at a proximal end thereof to provide additional closure forces to the opposing first 1915 and second 1920 jaws. The one or more redirect tubes 1950 are coupled to the closure system 2020. More particularly, distal ends of the upper and lower redirect tubes 1952, 1954 are coupled to proximal ends of an upper and lower portion of the closure system 2020, respectively. The upper and lower portions of the closure system 2020 include an axial passage extending therethrough, thereby allowing the upper and lower push coils 1982, 1984 to extend through the corresponding axial passage of respective upper and lower portions of the closure system 2020.

The closure system 2020 includes a ramp carriage 2030 and a closure cam 2040. The ramp carriage 2030, and more particularly a proximal end of the ramp carriage 2030, is coupled to a distal end of the one or more redirect tubes 1950. In particular, the distal end of the upper redirect tube 1952 is coupled to a proximal end of a top portion of the ramp carriage 2030 and the distal end of the lower redirect tube 1954 is coupled to a proximal end of a bottom portion of the ramp carriage 2030. The ramp carriage 2030 includes a ramp opening 2035. The ramp opening 2035 may be a slot or channel within the ramp carriage 2030, and is angled with respect to a longitudinal central axis of i) the one or more redirect tubes 1950 and/or ii) the top or bottom portions of the ramp carriage 2030.

The closure cam 2040 includes a pivot 2045, the pivot 2045 of the closure cam 2040 being disposed within the ramp opening 2035. More specifically, the pivot 2045 is slidably engaged within the ramp opening 2035, such that the closure cam 2040 can translate proximally downward and/or distally upward along the ramp opening 2035 of the ramp carriage 2030. An upper portion of the closure cam 2040 abuts a proximal end of one of the opposing first 1915 and second jaws 1920. In the example shown in FIG. 20, the upper portion of the closure cam 2040 abuts a proximal end of the second jaw 1920 (i.e., anvil jaw). The end effector 1905 also includes an anvil pivot 2050, which pivotally connects the first jaw 1915 and the second jaw 1920.

When a firing load on the firing cable 1935 increases, the increased load is coupled to the reaction cable 1945 and the redirect differential 1940, and the redirect differential 1940 applies increased force on the one or more redirect tubes 1950 in the proximal direction, which causes the closure system 2020 to induce additional rotation of one of the opposing first and second jaws 1915, 1920, thereby providing the additional closure forces to the opposing first and second jaws 1915, 1920. In particular, in one example, moving the one or more redirect tubes 1950 in the proximal direction causes the ramp carriage 2030 to move proximally, which causes the pivot 2045 of the closure cam 2040, and thus the entire closure cam 2040, to translate upward in the ramp opening 2035. Movement of the closure cam 2040 upwardly causes the upper portion of the closure cam 2040 to force the proximal end of the one of the opposing first and second jaws 1915, 1920 upward (in this case, the anvil jaw 1920), thereby providing the additional closure forces. More specifically, as the closure cam 2040 moves upward and pushes upwardly on the proximal end of the anvil jaw 1920, the anvil jaw 1920 pivots about the anvil pivot 2050, thereby causing the portion of the anvil jaw 1920 distally from the anvil pivot 2050 to rotate downwardly toward the lower jaw 1915, which results in additional compression/closure forces on the tissue being clamped. This action is seen in FIG. 20, where the anvil is in a "home" position at the top of FIG. 20 and in an "over clamp" position at the bottom of FIG. 20.

As stated above, pulling on the firing cable 1935 translates the firing carrier 1925 distally, which translates the push rods 1975, 1976 and push coils 1982, 1984 and knife body 1996 distally as well. As the knife body 1996 encounters resistance, the load on the firing cable 1935 increases, which increases the load on the reaction pulley 1930 that is connected to the floating redirect differential 1940 via the reaction cable 1945. The redirect differential 1940 applies load to the redirect tubes 1950 that are grounded to the closure mechanism 2020 described above. As shown in FIG. 20, the redirect tubes 1950 are grounded to a moveable ramp carriage 2030 that lifts the closure cam 2040 upon the application of the firing coupled load. This action induces additional rotation of the anvil jaw 1920 about the anvil pivot 2050 providing additional closure forces proportional to the firing load.

FIG. 21 depicts a perspective view of a firing redirect assembly according to another embodiment. In one embodiment, the firing redirect assembly 2100 is configured to be used with a surgical tool, such as surgical instrument 25010 described above, having an elongate shaft, such as elongate shaft 28000 described above, an end effector 2105, such as end effector 26000 or 1905 described above, and an articulation joint 2110, such as articulation joint 28200 or 1910 described above. The end effector 2105 is arranged at a distal end of the elongate shaft and includes opposing first 2115 and second 2120 jaws, such as first jaw 26100 and second jaw 26200 described above. The articulation joint 2110 interposes the end effector 2105 and the elongate shaft.

Similar to the firing redirect assembly 1900 described above with respect to FIGS. 19A and 19B, the firing redirect assembly 2100 of FIG. 21 includes a firing carrier 2125, a reaction pulley 2130, a firing cable 2135, a floating redirect differential 2140, a reaction cable 2145, and one or more redirect tubes 2150. The firing redirect assembly 2100 of FIG. 21 also includes push rods and push coils, similar to those described above for the firing redirect assembly 1900 of FIG. 19A. Since the components and operation of the firing system 2102 and firing redirect assembly 2100 of FIG. 21 are the same as the components and operation of the firing system 1902 and firing redirect assembly 1900 of FIGS. 19A and 19B described above, a detailed description thereof is omitted herein.

Together, the components of the firing redirect assembly 2100 redirect a portion of a firing force load applied to the firing cable 2135. That redirected firing force may be used to stabilize the articulation joint 2110. Specifically, a firing force applied to the firing cable 2135 in the proximal direction (i.e., a pulling force) translates the firing carrier 2125 distally, which translates the push rods and push coils and knife body distally as well. As the knife body encounters resistance, the load on the firing cable 2135 increases, which increases the load on the reaction pulley 2130 that is connected to the floating redirect differential 2140 via the reaction cable 2145. The redirect differential 2140 applies load to the redirect tubes 2150 that are grounded to the end effector 2105, as shown in FIG. 22. The firing system 2102 also includes a retract cable 2198 extending proximally from the firing carrier 2125, such that a pulling force on the retract cable 2198 by the upstream actuator causes the firing carrier 2125 to move proximally, which also causes the upper and lower push rods, the upper and lower push coils, and the knife body to translate proximally as well.

FIG. 22 depicts a side cross-sectional view of a portion of the firing redirect assembly 2100 of FIG. 21 according to one embodiment. As shown in FIG. 22, the redirect tubes 2150 are coupled to the end effector 2105. More specifically, distal ends of the redirect tubes 2150 are coupled to a proximal end of the end effector 2105. In this way, as the redirect differential 2140 applies load to the redirect tubes 2150 in the proximal direction, the redirect tubes 2150 pull the end effector 2105 in the proximal direction as well, compressing the articulation joint 2110 with additional force. In other words, when the firing load on the firing cable 2135 increases, the redirect differential 2140 applies increased force on the one or more redirect tubes 2150, which causes the articulation joint 2110 to compress and thereby stabilize the articulation joint 2110. In one embodiment, a force proportional to the firing force is provided to react firing loads through the articulation joint 2110. In another embodiment, the additional force of compression may be twice as much as the firing load applied to the firing cable 2135. Applying active tension to the redirect tubes 2150 also minimizes the level of buckling the flexible push coils can attain. As stated above, compressing and stabilizing the articulation joint 2110 in this way obviates the need for additional joint retention forces that would impart additional resistance, friction, drag, etc.

FIG. 23 depicts a perspective view of a firing redirect assembly according to another embodiment. In one embodiment, the firing redirect assembly 2300 is configured to be used with a surgical tool, such as surgical instrument 25010 described above, having an elongate shaft, such as elongate shaft 28000 described above, an end effector 2305, such as end effectors 26000, 1905, or 2105 described above, and an articulation joint 2310, such as articulation joint 28200 described above. The end effector 2305 is arranged at a distal end of the elongate shaft and includes opposing first 2315 and second 2320 jaws, such as first jaw 26100 and second jaw 26200 described above. The articulation joint 2310 interposes the end effector 2305 and the elongate shaft.

The articulation joint 2310 of FIG. 23 may be different than the articulation joints 1910, 2110 of FIGS. 19 and 20 above. Specifically, the articulation joint 2310 of FIG. 23 includes a series of movably interfacing annular disc members, similar to the series 28202 of movably interfacing annular disc members 28210 described above with regard to FIGS. 6-11. Similar to those described above, each annular disc member may include a "first" or proximal face that includes a centrally-disposed spherical feature or protrusion. Each annular disc member may further include a second or distal face that includes an annular hub portion that defines a concave socket therein. Each annular disc member further has a central, top, and bottom shaft passage or lumen therethrough to accommodate a reaction cable 2345 and upper and lower push coils, respectively. In at least one embodiment, the articulation joint 2310 further comprises a series of elastomeric annular spacer members that serve to space and provide elastic support between each annular disc member.

The firing system 2302 of the surgical instrument of FIG. 23 includes the same components as the firing system 1902 described above with respect to FIG. 19A, such as a firing cable 2335, firing carrier 2325, upper and lower push rods and coils, and knife body 2396. The structure and operation of the firing system 2302 is the same as discussed above, so a detailed explanation herein is omitted. The firing system 2302 also includes a retract cable 2398 extending proximally from the firing carrier 2325, such that a pulling force on the retract cable 2398 by the upstream actuator causes the firing carrier 2325 to move proximally, which also causes the upper and lower push rods, the upper and lower push coils, and the knife body 2396 to translate proximally as well.

The firing redirect assembly 2300 of the surgical instrument of FIG. 23 includes many, but not all, of the same components as the firing redirect assembly 1900 of FIG. 19A. As shown in FIG. 23, the firing redirect assembly 2300 includes the components of the firing system 2302 mentioned above as well as a reaction pulley 2330 and a reaction cable 2345. Together, these components redirect a portion of a firing force load applied to the firing cable 2335. That redirected firing force may be used to assist with closing the opposing first 2315 and second 2320 jaws, thereby reducing the required force to fire the surgical tool. The redirected firing force may also be used to compress, and thus stabilize, the articulation joint 2310 to minimize buckling and de-articulation.

Similar to above, the reaction pulley 2330 is disposed distally from the firing carrier 2325 and the firing cable 2335 is coupled to a distal end of the firing carrier 2325 and wraps around the reaction pulley 2330 and extends proximally past the firing carrier 2325 within the elongate shaft. The reaction cable 2345 is coupled to and extends between a distal end of the reaction pulley 2330 and a proximal end of the end effector 2305 of the surgical tool. The reaction cable 2345 extends through a central lumen 2350 of the articulation joint 2310, and a distal end of the reaction cable 2345 is coupled to a proximal bottom portion of the anvil jaw 2320, as shown and described below with respect to FIG. 24.

The differences between the firing redirect assembly 1900 of FIG. 19A and the firing redirect assembly 2300 of FIG. 23 is that the firing redirect assembly 2300 of FIG. 23 does not have a floating redirect differential or redirect tubes. Rather, the upper and lower push coils extend distally through upper and lower passages of the articulation joint 2310. Distal ends of the upper and lower push coils are coupled to upper and lower portions of the knife body 2396. The reaction cable 2345, rather than coupling to a redirect differential, extends through the central shaft passage or lumen 2350 of the annular disc members of the articulation joint 2310 and is coupled to a component of the end effector 2305 to cause rotation of the anvil jaw 2320.

For example, a firing load on the firing cable 2335 in a proximal direction causes the firing carrier 2325 to translate distally and causes the reaction pulley 2330 and the reaction cable 2345 to translate proximally, thereby assisting with closing the anvil jaw 2320 or assisting with stabilizing the articulation joint 2310 of the end effector 2305. In other words, the components of the firing redirect assembly 2300 redirect a portion of a firing force load applied to the firing cable 2135. That redirected firing force may be used to assist with closing the anvil jaw 2320, thereby reducing the required force to fire the surgical tool. The redirected firing force may also be used to stabilize the articulation joint 2310 to minimize buckling and de-articulation. Specifically, a firing force applied to the firing cable 2335 in the proximal direction (i.e., a pulling force) translates the firing carrier 2325 distally, which translates the push rods and push coils and knife body 2396 distally as well. As the knife body 2396 encounters resistance, the load on the firing cable 2335 increases, which increases the load on the reaction pulley 2330. This firing coupled load is transmitted through the articulation joint 2310 by the reaction cable 2345 and grounded to a closure mechanism, as shown in FIGS. 24 and 25 below.

FIG. 24 depicts a side cross-sectional view of a portion of the firing redirect assembly 2300 of FIG. 23 according to one embodiment. As shown in FIG. 24, the reaction cable 2345 extends through the central lumen 2350 of the articulation joint 2310, under a protrusion 2405 extending proximally from the proximal end of the jaws 2315, 2320, and a distal end of the reaction cable 2345 is coupled to a proximal bottom portion 2410, or arm, of the anvil jaw 2320. The anvil jaw 2320 is pivotably connected to the cartridge jaw at an anvil pivot 2420 in the upper proximal portion of the anvil jaw 2320.

When the firing load on the firing cable 2335 increases, a firing coupled load is applied to the reaction pulley 2330. The reaction cable 2345 transmits the firing coupled load through the articulation joint 2310 and causes additional rotation of the anvil jaw 2320 about the anvil pivot 2420 to provide an additional closure force to the anvil jaw 2320. In other words, a pulling force in the proximal direction by the reaction cable 2345 causes the proximal bottom portion 22410, or arm, of the anvil jaw 2320 to rotate counter-clockwise about the anvil pivot 2420, which causes the distal portion of the anvil jaw 2320 to also rotate downward counter-clockwise, thus further closing the anvil jaw 2320 toward the cartridge jaw 2315, which results in additional compression/closure forces on the tissue being clamped.

In another embodiment, a different closure mechanism may be used. FIG. 25 depicts a side cross-sectional view of a portion of the firing redirect assembly 2300 of FIG. 23 according to another embodiment. As shown in FIG. 25, the reaction cable 2345 extends through the central lumen 2350 of the articulation joint 2310, and a distal end of the reaction cable 2345 is coupled to a sliding cam wedge 2500 disposed under a proximal bottom portion 2510, or arm, of the anvil jaw 2320. The proximal end of the proximal bottom portion 2510, or arm, of the anvil jaw 2320 includes a downward facing protrusion 2520, or camming surface, extending downwardly from a bottom surface of the anvil jaw 2320 towards the cam wedge 2500.

The cam wedge 2500 may be generally wedge shaped and includes an inclined surface that extends upwardly in the distal direction. The camming surface 2520 of the proximal bottom portion 2510, or arm, of the anvil jaw 2320 is configured to contact and engage or abut the inclined surface of the cam wedge 2500. In this way, as the cam wedge 2500 moves proximally, the camming surface 2520 is pushed upwardly by the inclined surface of the cam wedge 2500, thus causing the anvil jaw 2320 to rotate counter-clockwise about the anvil pivot 2420. Conversely, as the cam wedge 2500 moves distally, the camming surface 2520 can slide down the inclined surface of the cam wedge 2500, thus allowing the anvil jaw 2320 to rotate clockwise about the anvil pivot 2420.

When the firing load on the firing cable 2335 increases, a firing coupled load is applied to the reaction pulley 2330. The reaction cable 2345 transmits the firing coupled load through the articulation joint 2310 and causes the sliding cam wedge 2500 to slide proximally which causes additional rotation of the anvil jaw 2320 about the anvil pivot 2420 to provide an additional closure force to the anvil jaw 2320. This redirected additional force helps reduce the required force to fire the surgical tool.

It should be appreciated that while the closure system 2020 of FIG. 20 includes a ramp carriage 2030 with a ramp opening 2035 configured to have a closure cam 2040 disposed therein, other types of closure mechanisms may be used. In one example, the closure mechanisms of FIGS. 24 and 25, such as the cam wedge 2500, may be used as the closure system 2020. Similarly, it should be appreciated that the closure mechanisms of FIGS. 24 and 25 could be swapped out with the closure system 2020 of FIG. 20. In another example, other types of closure systems and mechanisms may be used.

The redirected force also helps stabilize the articulation joint 2310, as described below with reference to FIG. 26. Specifically, a firing force applied to the firing cable 2335 in the proximal direction (i.e., a pulling force) translates the firing carrier 2325 distally, which translates the push rods and push coils and knife body 2396 distally as well. As the knife body 2396 encounters resistance, the load on the firing cable 2335 increases, which increases the load on the reaction pulley 2330. The firing coupled load is transmitted through the articulation joint 2310 by the reaction cable 2345 and grounded to the end effector 2305, as shown in FIG. 26.

FIG. 26 depicts a side cross-sectional view of a portion of the firing redirect assembly 2300 of FIG. 23 according to another embodiment. As shown in FIG. 26, the reaction cable 2345 is coupled to the end effector 2305. More specifically, a distal end of the reaction cable 2345 is coupled to a proximal end of the end effector 2305 by a coupler 2600. In this way, as the reaction pulley 2330 applies load to the reaction cable 2345 in the proximal direction, the reaction cable 2345 pulls the end effector 2305 in the proximal direction as well, compressing the articulation joint 2310 with additional force. In other words, when the firing load on the firing cable 2335 increases, a firing coupled load is applied to the reaction pulley 2330. The reaction cable 2345 transmits the firing coupled load through the articulation joint 2310 and causes the articulation joint 2310 to compress and thereby stabilize the articulation joint 2310. In one embodiment, a force proportional to the firing force is provided to react firing loads through the articulation joint 2310. In another embodiment, the additional force of compression may be twice as much as the firing load applied to the firing cable 2335. In other words, the joint 2310 may be compressed by two times the firing load. With the concentric disk joint 2310 of the embodiments discussed above, the high compression load at the articulation joint 2310 has the added benefit of inducing a potential frictional lock within the articulation joint 2310 to help counteract de-articulation forces.

The firing systems, articulation control systems, and the rotary drive systems discussed above may, for example, be motor-controlled and operated by one or more control circuits. For example, as mentioned above, the firing and retract cables discussed above may be controlled by an actuator or motor that are controlled by a control circuit of the surgical tool. The actuator or motor and control circuit may be supported within a housing of the surgical tools described above, such as in a handle portion, or may be located external to the surgical tools described above. The actuator or motor may be any suitable motor, electrically powered or otherwise by a power source and which may provide actuation to pull the firing and retract cables of the surgical tools disclosed herein.

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

FIG. 27 is a flowchart of an example method 2700 of operating a surgical tool according to one embodiment. In one embodiment, the method 2700 is implemented by the control circuit described above. It is noted, however, that the method 2700 may be implemented by other means.

The method 2700 may include applying a firing force to a firing cable (Block 2702). As described above, the firing force is applied to the firing cable by a motor or actuator disposed proximally from the firing carrier (i.e., upstream).

The method 2700 may further include coupling the firing force to a firing redirect assembly (Block 2704). The firing redirect assembly may include a firing carrier, a reaction pulley disposed distally from the firing carrier, the firing cable, and a reaction cable. The firing cable couples the firing carrier to the reaction pulley. The reaction pulley couples the firing cable to the reaction cable. Due to these couplings, the firing force applied to the firing cable is thereby coupled to the reaction cable.

The method 2700 may further include transmitting the coupled firing force through an articulation joint by the firing redirect assembly (Block 2706). As stated above, the firing force applied to the firing cable is coupled to the reaction cable, which extends into, and in some cases through, the articulation joint. In cases where the reaction cable does not extend entirely through the articulation joint, the reaction cable may be coupled to another component, such as a redirect differential described above, which in turn transmits the coupled firing force through the articulation joint. In the case of the redirect differential, the coupled firing force is transmitted through one or more redirect tubes through the articulation joint and coupled to the end effector, as described above with respect to FIGS. 19 and 20.

The method 2700 may further include providing an additional closure force to the anvil jaw of the end effector using the coupled firing force (Block 2708). In embodiments using the redirect differential and redirect tubes described above, the coupled firing force is transmitted to a closure system of the end effector to facilitate additional closing forces. One example of the closure system is shown and described above with respect to FIG. 20. Other types of closure systems may be used. In embodiments where the reaction cable extends entirely through the articulation joint, the reaction cable transmits the coupled firing force directly to the end effector to facilitate additional closing forces. Examples of embodiments in which the reaction cable assists with providing closure forces are shown and described above with respect to FIGS. 23-25.

The method 2700 may further include stabilizing the articulation joint using the coupled firing force (Block 2710). In one embodiment, the articulation joint may be stabilized by the coupled firing force being transmitted through one or more redirect tubes, as shown and described above with respect to FIGS. 19-22. In another embodiment, the articulation joint may be stabilized by the coupled firing force being transmitted through the articulation joint and coupled to the end effector by the reaction cable. In this example, the coupled firing force being applied to the end effector by the reaction cable compresses the articulation joint, thereby providing increased stabilization, as shown and described above with respect to FIGS. 23 and 26.

It should be appreciated that the foregoing embodiments allow for articulation joints of surgical staplers to react to increased firing loads during firing without negatively impacting joint performance. The foregoing embodiments utilize increased firing loads to increase the closure load on the anvil, which allows the force to fire to be reduced. In this way, energy is redistributed, or "captured," and used to improve the efficiency of firing and closure systems.

III. Examples of Combinations

The following examples/clauses relate to various non-exhaustive ways in which the teachings herein may be combined or applied. It should be understood that the following examples/clauses are not intended to restrict the coverage of any claims that may be presented at any time in this application or in subsequent filings of this application. No disclaimer is intended. The following examples/clauses are being provided for nothing more than merely illustrative purposes. It is contemplated that the various teachings herein may be arranged and applied in numerous other ways. It is also contemplated that some variations may omit certain features referred to in the examples/clauses below. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

1. A surgical tool, comprising:
an elongate shaft;
an end effector arranged at a distal end of the elongate shaft and including opposing first and second jaws;
an articulation joint interposing the end effector and the elongate shaft; and a firing redirect assembly including:
a firing carrier;
a reaction pulley disposed distally from the firing carrier;
a firing cable coupled to a distal end of the firing carrier and wrapping around the reaction pulley and extending proximally past the firing carrier within the elongate shaft;
a redirect differential disposed distally from the reaction pulley and proximally from the articulation joint;
a reaction cable coupled to and extending between a distal end of the reaction pulley and a proximal end of the redirect differential; and
one or more redirect tubes coupled to and extending between a distal end of the redirect differential and a proximal end of the end effector,
wherein a firing load on the firing cable in a proximal direction causes the firing carrier to translate distally and causes the reaction pulley, the reaction cable, the redirect differential, and the one or more redirect tubes to translate proximally.

2. The surgical tool of claim 1, further comprising:
an upper and lower push rod extending distally from the firing carrier; and
an upper and lower push coil coupled to and extending distally from the upper and lower push rods, respectively,
wherein the one or more redirect tubes comprise an upper and lower redirect tube,
wherein the upper and lower push coils extend distally through upper and lower portions of the redirect differential into the upper and lower redirect tubes, respectively, and
wherein distal ends of the upper and lower push coils are coupled to an upper and lower portion of a knife body, respectively.

3. The surgical tool of claim 2, wherein the firing load on the firing cable in the proximal direction causes the firing carrier, the upper and lower push rods, the upper and lower push coils, and the knife body to translate distally.

4. The surgical tool of claim 1, wherein the end effector includes a closure system at a proximal end thereof to provide additional closure forces to the opposing first and second jaws, and wherein the one or more redirect tubes are coupled to the closure system.

5. The surgical tool of claim 4, wherein when the firing load on the firing cable increases, the redirect differential applies increased force on the one or more redirect tubes, which causes the closure system to induce additional rotation of one of the opposing first and second jaws, thereby providing the additional closure forces to the opposing first and second jaws.

6. The surgical tool of claim 4, wherein the closure system comprises:
a ramp carriage coupled to a distal end of the one or more redirect tubes, the ramp carriage including a ramp opening; and
a closure cam including a pivot, the pivot of the closure cam being disposed within the ramp opening,
wherein an upper portion of the closure cam abuts a proximal end of one of the opposing first and second jaws.

7. The surgical tool of claim 6, wherein moving the one or more redirect tubes in the proximal direction causes the ramp carriage to move proximally, which causes the pivot of the closure cam to translate upward in the ramp opening and the upper portion of the closure cam to force the proximal end of the one of the opposing first and second jaws upward, thereby providing the additional closure forces.

8. The surgical tool of claim 1, wherein when the firing load on the firing cable increases, the redirect differential applies increased force on the one or more redirect tubes, which causes the articulation joint to compress and thereby stabilize the articulation joint.

9. The surgical tool of claim 2, wherein the redirect differential comprises:

an upper gear rack;

a lower gear rack; and a pinion gear in meshing engagement with the upper gear rack and the lower gear rack, such that when one of the upper gear rack or lower gear rack moves in one axial direction, the other of the upper gear rack or lower gear rack axially moves in an opposite direction.

10. The surgical tool of claim 9, wherein the upper gear rack accommodates the upper push coil and the lower gear rack accommodates the lower push coil, wherein during articulation, the pinion gear rotates causing the upper gear rack and lower gear rack to translate in opposite directions, thereby compensating for a change in path lengths of the upper push coil and lower push coil, respectively.

11. A firing redirect assembly for a surgical tool, the firing redirect assembly comprising:

a firing carrier;

a reaction pulley disposed distally from the firing carrier;

a firing cable coupled to a distal end of the firing carrier and wrapping around the reaction pulley and extending proximally past the firing carrier; and a reaction cable coupled to and extending between a distal end of the reaction pulley and a proximal end of an end effector of the surgical tool, the end effector including a cartridge jaw and an anvil jaw pivotably connected to the cartridge jaw at a pivot, wherein a firing load on the firing cable in a proximal direction causes the firing carrier to translate distally and causes the reaction pulley and the reaction cable to translate proximally.

12. The firing redirect assembly of claim 11, wherein the reaction cable extends through a central lumen of an articulation joint of the end effector, and wherein a distal end of the reaction cable is coupled to a proximal bottom portion of the anvil jaw.

13. The firing redirect assembly of claim 12, wherein when the firing load on the firing cable increases, a firing coupled load is applied to the reaction pulley, and wherein the reaction cable transmits the firing coupled load through the articulation joint and causes additional rotation of the anvil jaw about the pivot to provide an additional closure force to the anvil jaw.

14. The firing redirect assembly of claim 11, wherein the reaction cable extends through a central lumen of an articulation joint, and wherein a distal end of the reaction cable is coupled to a sliding cam wedge disposed under a proximal bottom portion of the anvil jaw.

15. The firing redirect assembly of claim 14, wherein when the firing load on the firing cable increases, a firing coupled load is applied to the reaction pulley, and wherein the reaction cable transmits the firing coupled load through the articulation joint and causes the sliding cam wedge to slide proximally which causes additional rotation of the anvil jaw about the pivot to provide an additional closure force to the anvil jaw.

16. The firing redirect assembly of claim 11, wherein when the firing load on the firing cable increases, a firing coupled load is applied to the reaction pulley, and wherein the reaction cable transmits the firing coupled load through an articulation joint and causes the articulation joint to compress and thereby stabilize the articulation joint.

17. A method of operating a surgical tool, the method comprising:

applying a firing force to a firing cable;

coupling the firing force to a firing redirect assembly;

transmitting the coupled firing force through an articulation joint by the firing redirect assembly; and providing an additional closure force to the anvil jaw of the end effector using the coupled firing force.

18. The method of claim 17, further comprising stabilizing the articulation joint using the coupled firing force.

19. The method of claim 18, wherein the firing redirect assembly comprises:

a firing carrier;

a reaction pulley disposed distally from the firing carrier;

a firing cable coupled to a distal end of the firing carrier and wrapping around the reaction pulley and extending proximally past the firing carrier; and a reaction cable coupled to and extending between a distal end of the reaction pulley and a proximal end of an end effector of the surgical tool, the end effector including a cartridge jaw and an anvil jaw pivotably connected to the cartridge jaw at a pivot.

20. The method of claim 19, wherein a distal end of the reaction cable is coupled to a proximal bottom portion of the anvil jaw, and wherein providing the additional closure force to the anvil jaw comprises:

transmitting the coupled firing force through the articulation joint by the reaction cable to the proximal bottom portion of the anvil jaw; and rotating the anvil jaw about the pivot using the coupled firing force.

21. The method of claim 19, wherein a distal end of the reaction cable is coupled to a sliding cam wedge disposed under a proximal bottom portion of the anvil jaw, and wherein providing the additional closure force to the anvil jaw comprises:

transmitting the coupled firing force through the articulation joint by the reaction cable to the sliding cam wedge;

sliding the sliding cam wedge proximally using the coupled firing force; and rotating the anvil jaw about the pivot via interaction of the proximal bottom portion of the anvil jaw with the sliding cam wedge.

22. The method of claim 19, wherein stabilizing the articulation joint using the coupled firing force comprises:

transmitting the coupled firing force through the articulation joint by the reaction cable to the proximal end of the end effector; and compressing the articulation joint using the coupled firing force.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. Pat. App. No. 63/467,622, entitled "Surgical Stapler Cartridge Having Intermediate Raised Tissue Engagement Protrusions," filed on May 19, 2023; U.S. Pat. App. No. 63/467,623, entitled "Surgical Stapler Cartridge Having Tissue Engagement Protrusions with Enlarged Engagement Surface," filed on May 19, 2023; U.S. Pat. App. No. 63/467, 648, entitled "Surgical Stapler Cartridge Having Raised Surface to Promote Buttress Adhesion," filed on May 19, 2023; U.S. Pat. App. No. 63/467,469, entitled "Surgical Stapler Cartridge Having Cartridge Retention Features," filed on May 19, 2023; U.S. Pat. App. No. 63/459,739, entitled "Surgical Stapler Anvil Having Staple Forming Pockets with Laterally Varying Orientations," filed on May 19, 2023; U.S. Pat. App. No. 63/467,656, entitled "Surgical Stapler With Discretely Positionable Distal Tip," filed on May 19, 2023; and/or U.S. Pat. App. No. 63/467,615, entitled "Incompatible Staple Cartridge Use Prevention Features for Surgical Stapler," filed on May 19, 2023.

Additionally, any one or more of the teachings herein may be combined with any one or more of the teachings disclosed in U.S. Pat. App. No. 63/459,739, entitled "Surgical Stapler Anvil Having Staple Forming Pockets with Laterally Varying Orientations," filed on Apr. 17, 2023. The disclosure of each of these U.S. patent applications is incorporated by reference herein in its entirety.

Additionally, any one or more of the teachings herein may be combined with any one or more of the teachings disclosed in U.S. Pat. No. 11,304,697, entitled "Surgical Stapler with Deflectable Distal Tip," issued Apr. 19, 2022, the disclosure of which is incorporated by reference herein, in its entirety; U.S. Pat. No. 11,317,912, entitled "Surgical Stapler with Rotatable Distal Tip," issued May 3, 2022, the disclosure of which is incorporated by reference herein, in its entirety; and/or U.S. Pat. No. 11,439,391, entitled "Surgical Stapler with Toggling Distal Tip," issued Sep. 13, 2022, the disclosure of which is incorporated by reference herein, in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as those made available by Auris Health, Inc. of Redwood City, CA or by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present disclosure, further adaptations of the methods and systems described herein may be accomplished by appropriate modifications by one of ordinary skill in the art without departing from the scope of the present disclosure. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present disclosure should be considered in terms of the following claims and is understood not to be limited to the details of structure and operation shown and described in the specification and drawings.

What is claimed is:

1. A surgical tool, comprising:
an elongate shaft;
an end effector arranged at a distal end of the elongate shaft and including opposing first and second jaws;
an articulation joint interposing the end effector and the elongate shaft; and
a firing redirect assembly including:
    a firing carrier;
    a reaction pulley disposed distally from the firing carrier;
    a firing cable coupled to a distal end of the firing carrier and wrapping around the reaction pulley and extending proximally past the firing carrier within the elongate shaft;
    a redirect differential disposed distally from the reaction pulley and proximally from the articulation joint;
    a reaction cable coupled to and extending between a distal end of the reaction pulley and a proximal end of the redirect differential; and
    one or more redirect tubes coupled to and extending between a distal end of the redirect differential and a proximal end of the end effector, wherein a firing load on the firing cable in a proximal direction causes the firing carrier to translate distally and causes the reaction pulley, the reaction cable, the redirect differential, and the one or more redirect tubes to translate proximally.

2. The surgical tool of claim 1, further comprising:

an upper and lower push rod extending distally from the firing carrier; and an upper and lower push coil coupled to and extending distally from the upper and lower push rods, respectively, wherein the one or more redirect tubes comprise an upper and lower redirect tube, wherein the upper and lower push coils extend distally through upper and lower portions of the redirect differential into the upper and lower redirect tubes, respectively, and wherein distal ends of the upper and lower push coils are coupled to an upper and lower portion of a knife body, respectively.

3. The surgical tool of claim 2, wherein the firing load on the firing cable in the proximal direction causes the firing carrier, the upper and lower push rods, the upper and lower push coils, and the knife body to translate distally.

4. The surgical tool of claim 2, wherein the redirect differential comprises:

an upper gear rack;

a lower gear rack; and a pinion gear in meshing engagement with the upper gear rack and the lower gear rack, such that when one of the upper gear rack or lower gear rack moves in one axial direction, the other of the upper gear rack or lower gear rack axially moves in an opposite direction.

5. The surgical tool of claim 4, wherein the upper gear rack accommodates the upper push coil and the lower gear rack accommodates the lower push coil, wherein during articulation, the pinion gear rotates causing the upper gear rack and lower gear rack to translate in opposite directions, thereby compensating for a change in path lengths of the upper push coil and lower push coil, respectively.

6. The surgical tool of claim 1, wherein the end effector includes a closure system at a proximal end thereof to provide additional closure forces to the opposing first and second jaws, and wherein the one or more redirect tubes are coupled to the closure system.

7. The surgical tool of claim 6, wherein when the firing load on the firing cable increases, the redirect differential applies increased force on the one or more redirect tubes, which causes the closure system to induce additional rotation of one of the opposing first and second jaws, thereby providing the additional closure forces to the opposing first and second jaws.

8. The surgical tool of claim 6, wherein the closure system comprises:

a ramp carriage coupled to a distal end of the one or more redirect tubes, the ramp carriage including a ramp opening; and a closure cam including a pivot, the pivot of the closure cam being disposed within the ramp opening, wherein an upper portion of the closure cam abuts a proximal end of one of the opposing first and second jaws.

9. The surgical tool of claim 8, wherein moving the one or more redirect tubes in the proximal direction causes the ramp carriage to move proximally, which causes the pivot of the closure cam to translate upward in the ramp opening and the upper portion of the closure cam to force the proximal end of the one of the opposing first and second jaws upward, thereby providing the additional closure forces.

10. The surgical tool of claim 1, wherein when the firing load on the firing cable increases, the redirect differential applies increased force on the one or more redirect tubes, which causes the articulation joint to compress and thereby stabilize the articulation joint.

11. A firing redirect assembly for a surgical tool, the firing redirect assembly comprising:

a firing carrier;

a reaction pulley disposed distally from the firing carrier;

a firing cable coupled to a distal end of the firing carrier and wrapping around the reaction pulley and extending proximally past the firing carrier; and a reaction cable coupled to and extending between a distal end of the reaction pulley and a proximal end of an end effector of the surgical tool, the end effector including a cartridge jaw and an anvil jaw pivotably connected to the cartridge jaw at a pivot, wherein a firing load on the firing cable in a proximal direction causes the firing carrier to translate distally and causes the reaction pulley and the reaction cable to translate proximally, and wherein when the firing load on the firing cable increases, a firing coupled load is applied to the reaction pulley, and wherein the reaction cable transmits the firing coupled load through an articulation joint and causes the articulation joint to compress and thereby stabilize the articulation joint.

12. The firing redirect assembly of claim 11, wherein the reaction cable extends through a central lumen of an articulation joint of the end effector, and wherein a distal end of the reaction cable is coupled to a proximal bottom portion of the anvil jaw.

13. The firing redirect assembly of claim 12, wherein when the firing load on the firing cable increases, a firing coupled load is applied to the reaction pulley, and wherein the reaction cable transmits the firing coupled load through the articulation joint and causes additional rotation of the anvil jaw about the pivot to provide an additional closure force to the anvil jaw.

14. The firing redirect assembly of claim 11, wherein the reaction cable extends through a central lumen of an articulation joint, and wherein a distal end of the reaction cable is coupled to a sliding cam wedge disposed under a proximal bottom portion of the anvil jaw.

15. The firing redirect assembly of claim 14, wherein when the firing load on the firing cable increases, a firing coupled load is applied to the reaction pulley, and wherein the reaction cable transmits the firing coupled load through the articulation joint and causes the sliding cam wedge to slide proximally which causes additional rotation of the anvil jaw about the pivot to provide an additional closure force to the anvil jaw.

16. A method of operating a surgical tool, the method comprising:

applying a firing force to a firing cable;

coupling the firing force to a firing redirect assembly;

transmitting the coupled firing force through an articulation joint by the firing redirect assembly;

providing an additional closure force to the anvil jaw of the end effector using the coupled firing force; and stabilizing the articulation joint using the coupled firing force.

17. The method of claim 16, wherein the firing redirect assembly comprises:

a firing carrier;

a reaction pulley disposed distally from the firing carrier;

a firing cable coupled to a distal end of the firing carrier and wrapping around the reaction pulley and extending proximally past the firing carrier; and a reaction cable coupled to and extending between a distal end of the reaction pulley and a proximal end of an end effector of the surgical tool, the end effector including a cartridge jaw and an anvil jaw pivotably connected to the cartridge jaw at a pivot.

18. The method of claim 17, wherein a distal end of the reaction cable is coupled to a proximal bottom portion of the anvil jaw, and wherein providing the additional closure force to the anvil jaw comprises:

transmitting the coupled firing force through the articulation joint by the reaction cable to the proximal bottom portion of the anvil jaw; and rotating the anvil jaw about the pivot using the coupled firing force.

19. The method of claim 17, wherein a distal end of the reaction cable is coupled to a sliding cam wedge disposed under a proximal bottom portion of the anvil jaw, and wherein providing the additional closure force to the anvil jaw comprises:

transmitting the coupled firing force through the articulation joint by the reaction cable to the sliding cam wedge;

sliding the sliding cam wedge proximally using the coupled firing force; and rotating the anvil jaw about the pivot via interaction of the proximal bottom portion of the anvil jaw with the sliding cam wedge.

20. The method of claim 17, wherein stabilizing the articulation joint using the coupled firing force comprises:

transmitting the coupled firing force through the articulation joint by the reaction cable to the proximal end of the end effector; and compressing the articulation joint using the coupled firing force.

* * * * *